US012622821B2

(12) United States Patent
Bewick-Sonntag et al.

(10) Patent No.: US 12,622,821 B2
(45) Date of Patent: May 12, 2026

(54) ABSORBENT ARTICLE

(71) Applicant: The Procter & Gamble Company, Cincinnati, OH (US)

(72) Inventors: Christopher Philip Bewick-Sonntag, Cincinnati, OH (US); John David Norcom, Cincinnati, OH (US); Shirdish Poondru, Cincinnati, OH (US); Matthew Howard Wasson, Cincinnati, OH (US); Rong Deng, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 254 days.

(21) Appl. No.: 18/198,303

(22) Filed: May 17, 2023

(65) Prior Publication Data

US 2023/0381032 A1 Nov. 30, 2023

Related U.S. Application Data

(60) Provisional application No. 63/480,335, filed on Jan. 18, 2023, provisional application No. 63/413,634, (Continued)

(51) Int. Cl.
*A61F 13/53* (2006.01)
*A61F 13/511* (2006.01)
(Continued)

(52) U.S. Cl.
CPC .......... *A61F 13/53* (2013.01); *A61F 13/5116* (2013.01); *A61F 13/514* (2013.01); (Continued)

(58) Field of Classification Search
CPC .... A61F 13/53; A61F 13/5116; A61F 13/514; A61F 13/534; A61F 2013/15406; (Continued)

(56) References Cited

U.S. PATENT DOCUMENTS

| | | | |
|---|---|---|---|
| 3,494,821 | A | 2/1970 | Evans |
| H163 | H | 11/1986 | Spraker et al. |

(Continued)

FOREIGN PATENT DOCUMENTS

| | | |
|---|---|---|
| CA | 2182570 C | 8/2000 |
| CA | 2239516 C | 5/2002 |

(Continued)

OTHER PUBLICATIONS

All Office Actions; U.S. Appl. No. 18/198,306, filed May 17, 2023.
(Continued)

*Primary Examiner* — Susan S Su
*Assistant Examiner* — Erin A Kim
(74) *Attorney, Agent, or Firm* — Anna E. Haller; Amanda Herman Berghauer

(57) ABSTRACT

A disposable absorbent article having a topsheet, a backsheet, and an absorbent core structure disposed therebetween. The absorbent core structure includes an upper nonwoven layer comprising polymer fibers and having a basis weight of from about 35 to about 85 gsm; a lower nonwoven layer comprising polymer fibers and having a basis weight of from about 10 to about 40 gsm; and an inner core layer disposed between the upper and lower nonwoven layers. The inner core layer comprises from about 50% to about 85% cellulosic fibers, by weight of the inner core layer, and from about 15% to about 50% superabsorbent particles, by weight of the inner core layer. The absorbent core structure has an average density of between about 0.045 $g/cm^3$ and about 0.15 $g/cm^3$. The inner core layer is contained within the nonwoven layers by substantially sealing at least a left and right side region of the upper and lower nonwoven layers.

20 Claims, 9 Drawing Sheets

Related U.S. Application Data filed on Oct. 6, 2022, provisional application No. 63/345,582, filed on May 25, 2022.

(51) Int. Cl.
| | |
|---|---|
| *A61F 13/514* | (2006.01) |
| *A61F 13/534* | (2006.01) |
| *A61F 13/15* | (2006.01) |

(52) U.S. Cl.
CPC .. *A61F 13/534* (2013.01); *A61F 2013/15406* (2013.01); *A61F 2013/530036* (2013.01); *A61F 2013/530489* (2013.01); *A61F 2013/53062* (2013.01); *A61F 2013/53445* (2013.01)

(58) Field of Classification Search
CPC ........ A61F 2013/530036; A61F 2013/530489; A61F 2013/53062; A61F 2013/53445; A61F 13/5323; A61F 13/47
See application file for complete search history.

(56) References Cited

U.S. PATENT DOCUMENTS

| | | | |
|---|---|---|---|
| 4,938,754 | A | 7/1990 | Mesek |
| 5,275,591 | A | 1/1994 | Mavinkurve |
| 5,458,592 | A | 10/1995 | Abuto et al. |
| 5,567,260 | A | 10/1996 | Mcfall |
| 5,591,148 | A | 1/1997 | Mcfall et al. |
| 5,611,790 | A | 3/1997 | Hines et al. |
| 5,756,039 | A | 5/1998 | Mcfall |
| 5,810,800 | A | 9/1998 | Hunter et al. |
| 5,928,452 | A | 7/1999 | Mcfall et al. |
| D413,669 | S | 9/1999 | Mcfall et al. |
| 5,964,689 | A | 10/1999 | Mcfall et al. |
| 6,045,544 | A | 4/2000 | Hershberger et al. |
| 6,183,587 | B1 | 2/2001 | Mcfall et al. |
| 6,203,654 | B1 | 3/2001 | Mcfall et al. |
| 6,261,277 | B1 | 7/2001 | Osborn, III et al. |
| 6,316,688 | B1 | 11/2001 | Hammons |
| 6,432,096 | B1 | 8/2002 | Mcfall et al. |
| 6,437,214 | B1 | 8/2002 | Everett et al. |
| 6,475,199 | B1 | 11/2002 | Gann et al. |
| 6,570,058 | B1 | 5/2003 | Fuchs et al. |
| 6,582,411 | B1 | 6/2003 | Carstens et al. |
| 6,702,796 | B2 | 3/2004 | Mcfall et al. |
| 6,899,701 | B2 | 5/2005 | Carstens et al. |
| 7,056,404 | B2 | 6/2006 | Mcfall et al. |
| 7,704,241 | B2 | 4/2010 | Rosenfeld et al. |
| 8,512,305 | B2 | 8/2013 | Dziezok et al. |
| 8,979,815 | B2 | 3/2015 | Roe et al. |
| 9,060,904 | B2 | 6/2015 | Hundorf et al. |
| 9,259,363 | B2 | 2/2016 | Dziezok et al. |
| 9,406,478 | B2 | 8/2016 | Birnbach et al. |
| 10,137,039 | B2 | 11/2018 | Stelzig et al. |
| 10,772,772 | B2 | 9/2020 | Michiels et al. |
| 11,464,385 | B2 | 10/2022 | Davis et al. |
| 2001/0014795 | A1 | 8/2001 | Kurata et al. |
| 2001/0026861 | A1* | 10/2001 | Takai .................... A61F 13/512 428/167 |
| 2001/0031358 | A1 | 10/2001 | Tan et al. |
| 2002/0151857 | A1 | 10/2002 | Bast et al. |
| 2003/0200991 | A1 | 10/2003 | Keck |
| 2005/0080391 | A1* | 4/2005 | Yoshimasa ............ A61F 13/534 604/385.01 |
| 2006/0135932 | A1 | 6/2006 | Abuto et al. |
| 2007/0044903 | A1 | 3/2007 | Wisneski et al. |
| 2007/0087169 | A1 | 4/2007 | Mcfall |
| 2007/0224903 | A1 | 9/2007 | Chakravarty et al. |
| 2007/0250026 | A1* | 10/2007 | Venturino ......... A61F 13/15634 604/383 |
| 2008/0167634 | A1 | 7/2008 | Kouta et al. |
| 2009/0131896 | A1 | 5/2009 | Ebitsuka et al. |
| 2010/0312206 | A1 | 12/2010 | Fujioka |
| 2011/0087185 | A1* | 4/2011 | Wohlke ............... A61F 13/8405 604/367 |
| 2011/0089593 | A1 | 4/2011 | Miyauchi et al. |
| 2013/0066290 | A1 | 3/2013 | Kawakami et al. |
| 2013/0211358 | A1 | 8/2013 | Kikkawa et al. |
| 2017/0119589 | A1 | 5/2017 | Bewick-sonntag |
| 2018/0001591 | A1 | 1/2018 | Dutkiewicz et al. |
| 2020/0297554 | A1 | 9/2020 | Petersen et al. |
| 2020/0315859 | A1 | 10/2020 | Denti et al. |
| 2020/0315871 | A1 | 10/2020 | Viens et al. |
| 2020/0315873 | A1 | 10/2020 | Viens et al. |
| 2020/0323709 | A1 | 10/2020 | Sillerström et al. |
| 2021/0292973 | A1 | 9/2021 | Rouse et al. |
| 2022/0104973 | A1 | 4/2022 | Viens et al. |
| 2022/0168158 | A1 | 6/2022 | Miller et al. |
| 2022/0387227 | A1 | 12/2022 | Kreisel et al. |

FOREIGN PATENT DOCUMENTS

| | | | |
|---|---|---|---|
| EP | 0812171 | B1 | 5/2000 |
| EP | 1075244 | B1 | 6/2003 |
| EP | 1504741 | A1 | 2/2005 |
| EP | 2572687 | B1 | 4/2016 |
| EP | 2630939 | B1 | 5/2020 |
| EP | 3799848 | A1 | 4/2021 |
| JP | 2016112404 | A | 6/2016 |
| JP | 2019034229 | A | 3/2019 |
| JP | 2021062176 | A | 4/2021 |
| JP | 2021083542 | A | 6/2021 |
| JP | 2021097845 | A | 7/2021 |
| WO | 200641507 | A1 | 7/2017 |
| WO | 2017115541 | A1 | 7/2017 |
| WO | 2017207135 | A1 | 12/2017 |
| WO | 2020205946 | A1 | 10/2020 |

OTHER PUBLICATIONS

All Office Actions; U.S. Appl. No. 18/198,307, filed May 17, 2023.
Unpublished U.S. Appl. No. 18/198,306, filed May 17, 2023, to Christopher Philip Bewick-Sonntag et al.
Unpublished U.S. Appl. No. 18/198,307, filed May 17, 2023, to Christopher Philip Bewick-Sonntag et al.
PCT Search Report and Opinion for PCT/US2023/022452 dated Sep. 7, 2023;12 pages.

* cited by examiner

ABSORBENT ARTICLE

CROSS REFERENCE TO RELATED APPLICATIONS

This application claims the benefit of U.S. Provisional Application No. 63/345,582, filed May 25, 2022, and U.S. Provisional Application No. 63/413,634, filed Oct. 6, 2022, and U.S. Provisional Application No. 63/480,335, filed Jan. 18, 2023, the entire disclosures of which are fully incorporated by reference herein.

FIELD OF THE INVENTION

The present invention pertains to an absorbent article with conforming features as well as improved resilient structures.

BACKGROUND OF THE INVENTION

Absorbent articles are widely used among consumers, e.g., diapers, training pants, feminine pads, adult incontinence pads, etc. Generally, absorbent articles such as these comprise a topsheet and a backsheet, with an absorbent core structure disposed therebetween. Historically, absorbent core structures for menstrual pad applications utilize cellulose fibers in various ways to manage the complex and varied rheological properties of menstrual fluid and vaginal discharge.

The first approach included cellulose (also known as "fluff" or "pulp") based thick absorbent cores that can be stiff, bulky, and suffer from structural collapse due to the short fiber lengths of cellulose (<2.5 mm), particularly when loaded with fluid due to cellulose fiber softening when wet. Over time, these thick cellulose rich absorbent cores have been made thinner with the inclusion of absorbent polymer materials, such as absorbent gelling material ("AGM"), to further boost their absorption properties. However, these absorbent core structures are less mechanically strong and even less able to retain their shape, particularly when loaded with liquid exudate. These absorbent core structures can form cracks and tears while in-use and bunch (a permanent deformed shape). These thinner structures tend to be even more densified (thus stiffer) and are often wrapped in a simple cellulose tissue or thin nonwoven layer to keep the AGM inside and reduce core tearing and undesirable bunching while in use.

Other approaches combine these wrapped cellulose and AGM cores with an additional fluid acquisition-distribution layer (above the fluid storage core) to further improve the performance of these simple wrapped cores. This additional acquisition-distribution layer further serves to improve integrity and to some degree tearing and bunching of the wrapped core. These acquisition-distribution layers, however, are not ideal for complex viscous fluids which need to move over the boundary between these layers. To better facilitate fluid partitioning from the acquisition-distribution system to the fluid storage wrapped cellulose and AGM core, the core can be densified to increase capillarity and the ability to pull fluid effectively from the acquisition-distribution layer above. However, densifying this absorbent system comes at the cost of comfort (stiffness) and the ability of the absorbent core structure and/or absorbent article to readily conform to the wearer's unique anatomical geometry.

Another material used in the absorbent core structure includes an airlaid core. Airlaid cores are typically composed of cellulose, AGM, and synthetic binder fibers to enhance wet integrity and often a surface coating of a polymer (such as latex) to reduce dust during product manufacture. Because these materials are manufactured at a separate supplier offline and need to be transported and introduced into a fast-moving production line, they are highly densified and stiff. The densification and synthetic binder fibers provide a higher wet integrity in-use and can help facilitate fluid transport from the acquisition-distribution layer to the airlaid core due to higher capillarity. However, this again can be at the cost of comfort (stiffness) and the ability to readily conform to the wearer's unique anatomical geometry due to high bending stiffness.

As such, it would be beneficial to have an improved absorbent article comprising an absorbent core structure which addresses the tradeoff of comfortable conformance and wet resiliency while maintaining good absorbency properties. And, it would be beneficial to provide a method for creating such articles without sacrificing performance properties of the products.

SUMMARY OF THE INVENTION

Disclosed herein is a disposable absorbent article comprising: a topsheet; a backsheet; and an absorbent core structure disposed between the topsheet and backsheet, wherein the absorbent core structure comprises: an upper nonwoven layer comprising polymer fibers and having a basis weight of from about 35 gsm to about 85 gsm; a lower nonwoven layer comprising polymer fibers and having a basis weight of from about 10 gsm to about 40 gsm; and an inner core layer disposed between the upper nonwoven layer and the lower nonwoven layer, wherein the inner core layer comprises from about 50% to about 85% cellulosic fibers, by weight of the inner core layer, and from about 15% to about 50% superabsorbent particles, by weight of the inner core layer; wherein the absorbent core structure has an average density of between about 0.045 g/cm3 and about wherein the inner core layer is contained within the upper nonwoven layer and the lower nonwoven layer by substantially sealing at least a left side region and a right side region of the upper nonwoven layer and the lower nonwoven layer at a perimeter seal.

Also disclosed herein is a disposable absorbent article comprising: a topsheet; a backsheet; and an absorbent core structure disposed between the topsheet and backsheet, wherein the absorbent core structure has a front region, a middle region, and a back region and comprises: an upper nonwoven layer comprising polymer fibers and having a basis weight of from about 35 gsm to about 85 gsm; a lower nonwoven layer comprising polymer fibers and having a basis weight of from about 10 gsm to about 40 gsm; and an inner core layer disposed between the upper nonwoven layer and the lower nonwoven layer; wherein the inner core layer comprises a mixture of cellulosic fibers and superabsorbent particles, wherein the absorbent core structure comprises a plurality of structural bond sites; wherein the structural bond sites have a bond area of from about 2 mm$^2$ to about 5 mm$^2$, and wherein the total structural bond area of the absorbent core structure is from about 0.75% to about 4.5% of the absorbent core structure as measured according to the Structural Bond Sites Pattern Spacing and Area Measurement Method.

DETAILED DESCRIPTION OF THE INVENTION

Figures 1, 2A:
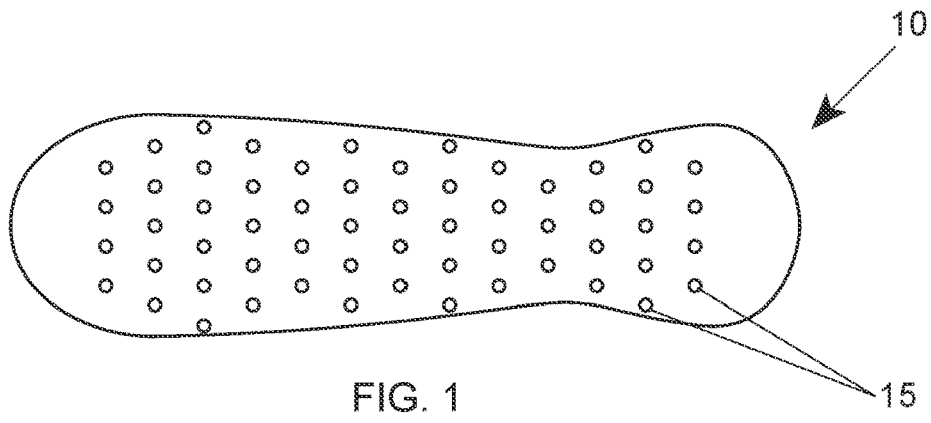
FIG. 1 is a representation of an absorbent core structure in accordance with the present disclosure.
FIG. 2A is a representation of an absorbent article in accordance with the present disclosure.

As used herein "disposable absorbent article" or "absorbent article" shall be used in reference to articles such as diapers, training pants, diaper pants, refastenable pants, adult incontinence pads, adult incontinence pants, feminine hygiene pads, cleaning pads, and the like, each of which are intended to be discarded after use.

As used herein "absorbent core structure" shall be used in reference to the upper nonwoven layer, the lower nonwoven layer, and the inner core layer disposed between the upper nonwoven layer and the lower nonwoven layer.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, the term "filament" refers to any type of continuous strand produced through a spinning process, a meltblowing process, a melt fibrillation or film fibrillation process, or an electrospinning production process, or any other suitable process to make filaments. The term "continuous" within the context of filaments are distinguishable from staple length fibers in that staple length fibers are cut to a specific target length. In contrast, "continuous filaments" are not cut to a predetermined length, instead, they can break at random lengths but are usually much longer than staple length fibers.

As used herein, "machine direction" refers to the direction in which a web flows through an absorbent article converting process. For the sake of brevity, may be referred to as "MD".

As used herein, "cross machine direction" refers to the direction which is perpendicular to the MD. For the sake of brevity, may be referred to as "CD".

As used herein, "resilient" refers to a material that tends to retain its shape both in the dry and wet states and when subjected to a compression force tends to recover its original, pre-compression shape when such force is removed. In some aspects, the upper and/or lower nonwoven layers described herein may be resilient.

As used herein, "wearer-facing" (sometimes referred to herein as body-facing) and "outward-facing" (sometimes referred to herein as garment-facing) refer respectively to the relative location of an element or a surface of an element or group of elements. "Wearer-facing" implies the element or surface is nearer to the wearer during wear than some other element or surface. "Outward-facing" implies the element or surface is more remote from the wearer during wear than some other element or surface (i.e., element or surface is proximate to the wearer's garments that may be worn over the absorbent article).

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The disposable absorbent articles described herein comprise a topsheet, a backsheet, and an absorbent core structure which comprises an upper nonwoven layer and a lower nonwoven layer, with an inner core layer disposed between the upper and lower nonwoven layers. The inner core layer may be contained within the nonwoven layers by substantially sealing at least the left side and the right side region of the upper and lower nonwoven layers at a perimeter seal. In some configurations, the upper and lower nonwoven layers may be joined at a perimeter seal which extends around the entire perimeter of the inner core layer.

In some configurations, the disposable absorbent article may comprise the following structure (from a wearer-facing surface to an outward-facing surface): a topsheet, an upper nonwoven layer, an inner core layer, a lower nonwoven layer, and a backsheet. In some aspects, the topsheet may be in direct contact with the upper nonwoven layer, the upper nonwoven layer may be in direct contact with the inner core layer, and/or the inner core layer may be in direct contact with the lower nonwoven layer. By "direct contact", it is meant that there is no further intermediate component layer between the respective layer in direct contact thereto. It is however not excluded that an adhesive material may be disposed between at least a portion of the layers described above.

Figure 3:
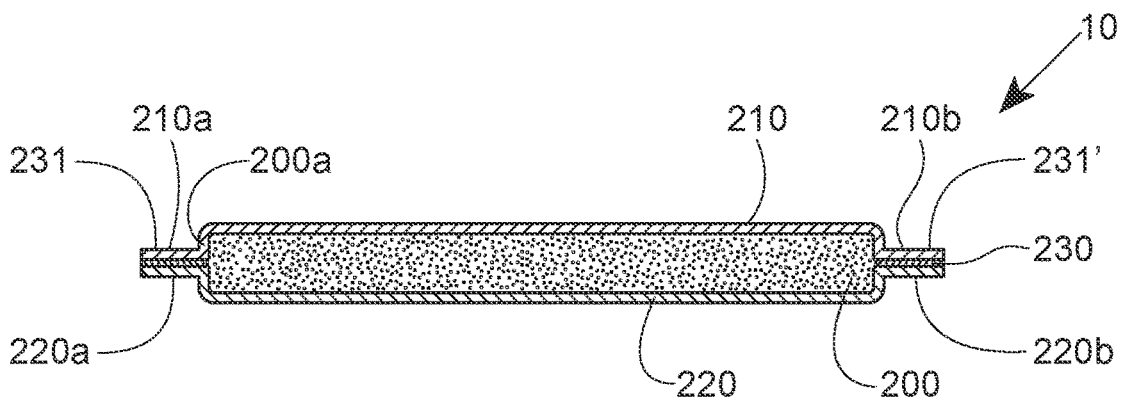
FIG. 3 is a cross section of the absorbent core structure.

As shown in FIGS. 1 and 3, absorbent core structure 10 may comprise an upper nonwoven layer 210 and a lower nonwoven layer 220 (also referred to herein collectively as upper and lower nonwoven layers or upper and lower nonwovens) and an inner core layer 200 disposed between the upper nonwoven layer 210 and the lower nonwoven layer 220. The absorbent core structure 10 may comprise inner core layer 200 comprising a liquid-absorbent material. Without being limited by theory, it is believed that the absorbent core structure may recover its shape dry or wet across a range of bodily movements and compressions. The liquid absorbent material may comprise a matrix comprising cellulosic fibers and superabsorbent particles, sometimes referred to herein as "fluff/AGM". The upper and lower nonwoven layers 210, 220 may be joined together at a perimeter seal 230 with glue or other conventional bonding methods including, but not limited to, ultrasonic bonding, fusion bonding, crimping, and combinations thereof.

The flexibility and/or resiliency of the absorbent core structure results in an absorbent article that comfortably conforms to the wearer's anatomical geometry while efficiently managing the fluid as it exits the body. This can, unexpectedly, be achieved without typical densification stiffening (for wet integrity) by leveraging resilient upper and lower nonwoven layers composed of resilient polymers located above and below the loosely packed fluff/AGM matrix of the inner core layer. This absorbent core structure is able to carry the structural load and recover shape without physically being stiff or losing the desired structural properties when the absorbent core structure becomes wet.

It is believed that wet integrity/shape stability in a cellulose rich absorbent core structure without substantial densification and stiffening results when select resilient upper and lower nonwovens are positioned above and below the fluff/AGM matrix of the inner core layer and joined to and around the fluff/AGM matrix. The upper and lower nonwovens require sufficient recovery force to carry the fluff/AGM matrix back to the original state or a stable fiber orientation state following compression. Wrapping or encapsulating a cellulose rich fluff core with a simple cellulose tissue or less resilient nonwoven material may not exhibit sufficient recovery energy to recover shape in-use and particularly when wetted. Structural, wet resilient nonwovens detailed herein may exhibit recovery energies following compression that are sufficient to recover the cellulose rich fiber matrix and are chosen to deliver high compression recovery, with relatively low stiffness, in both dry and wet states.

Suitable upper nonwoven layers may have a basis weight of from about 30 gsm to about 85 gsm, or from about 35 gsm to about 70 gsm, or from about 40 to about 60 gsm. The upper nonwoven layer may have a Tensile Stiffness of from about 0.3 N/mm to about 1.6 N/mm. The upper nonwoven layer may have a Strain to Break of greater than about 10%, or from about 10% to about 50%, or from about 20% to about 40%. The upper nonwoven layer may have a Permanent Strain of about 0.005 to about 0.013 mm/mm, or from 0.005 to about 0.0090 mm/mm.

Suitable lower nonwoven layers may have a basis weight of from about 10 to about 40 gsm, or from about 15 to about 20 gsm. The lower nonwoven layer may have a Tensile Stiffness of from about 0.2 N/mm to about 1.6 N/mm. The lower nonwoven layer may have a Strain to Break of greater than about 10%, or from about 10% to about 50%, or from about 20% to about 40%. The lower nonwoven layer may have a Permanent Strain of about 0.005 to about 0.013 mm/mm.

The upper and lower nonwoven layers may comprise polymer fibers. Suitable upper and lower nonwoven fibers may be selected from PET (polyethylene terephthalate), PP (polypropylene), a BiCo (Bicomponent fiber) selected from PE/PP (PE sheath and PP core) and/or PE/PET (PE sheath PET core), PLA (polylactic acid), and combinations thereof.

Suitable upper nonwovens may comprise from about 60 to about 100%, or from about 70% to about 100% synthetic fibers, or from about 0 to about 40%, or from about 0 to about 30% regenerated cellulosic fibers, such as rayon and/or viscose.

The upper nonwoven layer may comprise fibers having a staple length of greater than about mm, or greater than about 25 mm, or from about 10 mm to about 100 mm, or from about 20 mm to about 75 mm, or from about 25 mm to about 50 mm. The upper nonwoven layer may comprise fibers having a fiber diameter of from about 1.3 DTex to about 10 DTex, alternatively from about 1.3 DTex to about 6.0 DTex, alternatively from about 2.0 DTex to about 5.0 DTex. In some configurations, the upper nonwoven layer may comprise fibers, wherein the fibers are a blend of staple fibers having a fiber diameter of from about 2.0 DTex to about 10 DTex.

The lower nonwoven layer may comprise fibers having a length of greater than about 10 mm, or greater than about 25 mm, or from about 10 mm to about 100 mm, or from about 20 mm to about 75 mm, or from about 25 mm to about 50 mm. In some configurations, the lower nonwoven layer may comprise continuous fibers. The lower nonwoven layer may comprise fibers having a fiber diameter of from about 1.3 DTex to about 5.0 DTex, alternatively from about 1.3 DTex to about 3.3 DTex, alternatively from about 1.3 DTex to about 2.2 DTex, alternatively from about 2.0 DTex to about 10 DTex. In some configurations, the lower nonwoven layer may comprise fibers, wherein the fibers are a blend of fibers having a fiber diameter of from about 0.1 DTex to about 6.0 DTex.

In some configurations, suitable fiber combinations may include upper nonwoven polymer fibers having a diameter of from about 2.0 DTex to about 10 DTex and lower nonwoven polymer fibers having a diameter of from about 1.7 DTex to about 5 DTex. In some configurations, suitable fiber combinations may include upper nonwoven polymer fibers having a diameter of from about 1.3 DTex to about 2.2 DTex and lower nonwoven polymer fibers having a diameter of from about 1.7 DTex to about 5 DTex.

Referring to FIGS. 2A and 3, absorbent article 20 may comprise an absorbent core structure comprising an upper nonwoven layer 210 and a lower nonwoven layer 220 with an inner core layer 200 disposed therebetween. FIG. 2A is a top view of absorbent article 20 with the topsheet removed for simplicity. FIG. 3 is a cross section view of absorbent core structure 10.

Absorbent article 20 and absorbent core structure 10 each include a front region 21, a back region 23, and a middle region 22 disposed intermediate the front region and the back regions. Upper nonwoven layer 210 may comprise a left side region 210a and a right side region 210b, and lower nonwoven layer 220 may comprise a left side region 220a and a right side region 220b. The upper and lower nonwoven layers 210, 220 may extend outwardly from an inner core layer perimeter 200a and may be joined together to form a perimeter seal 230. In some configurations, the entire inner core layer 200 may be located inboard of the perimeter seal 230. The perimeter seal 230 may help to seal the absorbent material of the inner core layer 200 inside the upper and lower nonwoven layers 210, 220. Perimeter seal 230 may comprise at least a first lateral seal region 231 and a second lateral seal region 231'. In some configurations, perimeter seal 230 may further comprise a front perimeter seal region 232 and/or a back perimeter seal region 233. In some configurations, the perimeter seal 230 may extend around the entire inner core layer perimeter 200a. In some configurations, the perimeter seal 230 may extend partially around the inner core layer perimeter 200a.

In some configurations, the inner core layer 200 may be contained within the upper nonwoven layer 210 and the lower nonwoven layer 220 by substantially sealing at least a left side region 210a, 220a and a right side region 210b, 220b of the upper nonwoven layer 210 and the lower nonwoven layer 220. In some configurations, the inner core layer 200 may be contained within the upper nonwoven layer 210 and the lower nonwoven layer 220 by sealing at least a portion of the left side region 210a, 220a and the right side region 210b, 220b of the upper nonwoven layer 210 and the lower nonwoven layer 220.

The perimeter seal 230 may have a seal width WS of between about 1 mm and about 10 mm, or between about 2 mm and about 8 mm, or between about 3 mm and 6 mm. The seal width WS may be uniform or may vary about the perimeter of the inner core layer.

In some configurations, the absorbent article 20 may also comprise a front end seal 234 positioned in a front end region 227 of the absorbent article and a back end seal 235 positioned in a back end region 228 of the absorbent article. The front end seal 234 and/or back end seal 235 may seal the topsheet, upper nonwoven layer, lower nonwoven layer, and the backsheet together. In some configuration, the front end seal 234 and/or the back end seal 235 may seal the topsheet and the backsheet. In some configurations, the front end seal 234 and/or the back end seal 235 may be a crimp seal.

In some configurations, the upper and lower nonwoven layers 210, 220 may be discrete materials that can be cut to approximately the size and shape of the inner core layer 200 so as to fit between the topsheet and backsheet but may not extend substantially into either the front end seal 234 or the back end seal 235. In some configurations, the inner core layer 200, upper nonwoven layer 210 and/or lower nonwoven layer 220 may be shaped, meaning it is non-rectangular. In some configurations, the upper and/or lower nonwoven layers 210, 220 may extend from the front end region 227 of the absorbent article, through the front end seal 234 and the back end seal 235, to the back end region 228 of the absorbent article.

Nonwoven layers comprising polymer fibers may hold their shape and resist plasticizing when wet when attached to the fluff/AGM matrix through the application of a core construction adhesive that is applied either directly to the fluff/AGM matrix or the resilient nonwoven layer via a conventional spray coating application chosen to achieve a bond but not disrupt the flow of fluid to the fluff/AGM matrix. Additionally, the upper and lower nonwoven layers 210, 220 may have at least a partial perimeter seal 230 to better connect the upper and lower nonwoven layers 210, 220 with the inner core layer 200 contained within the upper and lower nonwoven layers 210, 220. The perimeter seal 230 may be positioned in at least the middle region 22 of the absorbent article 20 and/or the absorbent core structure 10. Without being limited by theory, it is believed that the middle region 22 (located between the wearer's thighs during use) may be subjected to the most frequent and/or highest forces during use. It was found that the presence of at least a partial perimeter seal at a left side region and a right side region of the upper nonwoven layer and the lower nonwoven layer external to the fluff/AGM matrix, where the upper and lower nonwoven layers are bonded by conventional means (e.g., adhesives, polymer welding, and/or strong physical entanglement), may help to ensure the upper and lower nonwovens maintain their structural function during physical deformations without separating, limiting any potential integrity and bunching issues. Creating a perimeter seal may allow for any excess nonwoven material to be removed to enable an absorbent core structure to be shaped to conform to inner thigh geometry.

Suitable upper and lower nonwoven layer materials may bend and recover their original shape following the bending force Flimsy or highly flexible materials readily bend at low peak force (load) and with low bending energy. Unsuitable materials, while readily bending, do not have sufficient recovery energy and so retain a deformed, bent state because of insufficient recovery energy. Suitable materials have sufficient energy to recover their initial pre-bent state. The materials with sufficient bending recovery energy may be considered resilient upper and lower nonwoven layers.

As noted above, the upper and lower nonwovens may include polymer fibers. Polymer fibers may be included to help provide structural integrity to the upper and lower nonwovens. The polymer fibers may help increase structural integrity of the upper and lower nonwovens in both a machine direction (MD) and in a cross-machine direction (CD), which may facilitate web manipulation during processing of the upper and lower nonwovens for incorporation into a pad.

Polymer fibers of any suitable composition may be selected. Some examples of suitable polymer fibers may include bi-component fibers comprising polyethylene (PE) and polyethylene terephthalate (PET) components or polyethylene terephthalate and co-polyethylene terephthalate components. The components of the bi-component fiber may be arranged in a sheath-core configuration, a side-by-side configuration, an eccentric sheath-core configuration, a trilobal arrangement, or any other desired configuration. In some configurations, the polymer fibers may include bi-component fibers having PE/PET components arranged in a concentric, sheath-core configuration, wherein the polyethylene component forms the sheath.

While other materials may be useful in creating a resilient structure, it is believed that the stiffness of a PET core component in a sheath-core fiber configuration is useful for imparting resilience to the upper and lower nonwovens. In synergistic combination, a PE sheath component, having a lower melting temperature than the PET core component, may be utilized to provide inter-fiber melt/fusion bonding, effected via heat treatment of the precursor batt. This can help provide tensile strength to the web in both the MD and CD. Such inter-fiber bonds may serve to reduce fiber-to-fiber sliding, and thereby further contribute to imparting shape stability and resiliency to the material even when it is wetted.

Where a relatively higher weight fraction of polymer fibers is included, more connections within the structure may be created via heat treatment. However, too many connection points may impart greater stiffness to the upper and lower nonwovens than may be desirable. For this reason, selecting the weight fraction of the polymer fibers may involve prioritizing and balancing competing needs for stiffness and softness in the upper and lower nonwovens.

As noted above, the upper and lower nonwovens may additionally include polymer fibers which increase resiliency of the upper and lower nonwovens. The resilient polymer fibers may help the upper and lower nonwovens maintain permeability and compression recovery. In some configurations, the upper and lower nonwovens may comprise resilient polymer fibers having varying cross sections, e.g., round and hollow spiral, and/or may comprise resilient fibers having varying sizes.

The polymer fibers may be resilient and may be spun from any suitable thermoplastic resin, such as polypropylene (PP), polyethylene terephthalate (PET), or other suitable thermoplastics known in the art. The average staple length of the resilient polymer fibers may be selected to be in the range of greater than about 10 mm, from about 20 mm to about 100 mm, or about 30 mm to about 50 mm, or about 35 mm to about 50 mm. The resilient polymer fibers may have any suitable structure or shape. For example, the resilient polymer fibers may be round or have other shapes, such as spiral, scalloped oval, trilobal, scalloped ribbon, and so forth. Further, the resilient polymer fibers may be solid, hollow, or multi-hollow. The resilient polymer fibers may be solid and round in shape. In other suitable examples, resilient polymer fibers may include polyester/co-extruded polyester fibers. Other suitable examples of resilient polymer fibers may include bi-component fibers such as polyethylene/polypropylene, polyethylene/polyethylene terephthalate, polypropylene/polyethylene terephthalate bicomponent fibers. These bi-component fibers may have a sheath/core configuration.

The resilient polymer fibers may also be polyethylene terephthalate (PET) fibers, or other suitable non-cellulosic fibers known in the art. PET fibers may be imparted with any suitable structure or shape. For example, the PET fibers may be round or have other shapes, such as spiral, scalloped oval, trilobal, scalloped ribbon, hollow spiral, and so forth. The PET fibers may be solid, hollow or multi-hollow. In one particular example, PET fibers may be hollow in cross section and have a curl or spiral configuration along their lengths. Optionally, the resilient polymer fibers may be spiral-crimped or flat-crimped. The resilient polymer fibers may have an average crimp count of about 4 to about 12 crimps per inch (cpi), or about 4 to about 8 cpi, or about 5 to about 7 cpi, or about 9 to about 10 cpi. Particular non-limiting examples of resilient polymer fibers may be obtained from Wellman, Inc. (Ireland) under the trade designations H1311 and T5974. Other examples of suitable resilient polymer fibers are disclosed in U.S. Pat. No. 7,767,598.

The stiffening polymer fibers and resilient polymer fibers should be carefully selected. For example, while the constituent polymers forming the stiffening polymer fibers and the resilient polymer fibers may have similarities, resilient polymer fiber composition should be selected such that their constituents' melting temperature(s) is/are higher than that of the bondable components of the stiffening polymer fibers. Otherwise, during heat treatment, resilient polymer fibers could bond to stiffening polymer fibers and vice versa, and thereby an overly rigid structure. To avoid this risk where the stiffening polymer fibers include bicomponent fibers, e.g., core-sheath configuration fibers with a sheath component of relatively lower melting temperature at which fusion bonding will occur, the resilient polymer fibers may comprise the constituent chemistry of only the core, which may be a polymer having a relatively higher melting temperature.

Nonwoven performance can be impacted by a combination of the nonwoven fiber polymer choice, fiber properties and how the fibers are arranged or connected. Nonwoven selection can impact the absorbent article's ability to recover its shape following compression, bending and extension (stretching) forces present in-use with body motion. If the fibers are short fibers (less than about 10 mm) then they are likely to irreversibly rearrange under extension and compressive forces. The rearranging (changing their orientation/state) of fibers in a fiber matrix dissipates the tensile (elongation) or compressive forces so that the energy used to affect the deformation is no longer available for recovery to the original shape. Longer fiber networks (typically greater than about 10 mm but less than about 100 mm) can dissipate the tensile/compressive forces typical of bodily motions along the fiber length and across the structure. As a result, the imparted forces are available to recover the structure to its original state. Longer fiber networks composed of finer fibers (less than about 15 to about 20 microns and about 2.0 DTex) more readily elongate and compress. As a result, the fluff/AGM structure can deform more readily (and to a higher degree) but the energy associated with these deformations is relatively small and insufficient to carry the structure back to its original state. Thicker fiber, such as greater than about 2.0 DTex to about 10 DTex, are both flexible under bodily forces but provide sufficient fiber and web recovery energy to return the structure to its original state.

The fiber arrangement in a long fiber network from a structural standpoint can impact the performance of the absorbent articles containing these nonwovens. Long fiber webs of thicker fibers are typically loftier than a conventional thin spunbond nonwoven web composed of continuous fine fibers that are closely spaced and physically bonded together. Creating a web of thicker fibers arranged in a more randomized orientation such as those that can be achieved via carding, hydro-entangling and needling are able to elongate and compress, whereby the fibers only temporary adjust their arrangement (space between the fibers exist for these arrangements) and are able to carry/store the deformation forces and this energy is available for recovering the structural shape.

Additionally finer (less than about 2.0 DTex) synthetic fibers such as BiCo and PP fibers commonly found in spunbond are closely spaced, relatively parallel aligned and closely bonded together. The bonded fibers within these spunbond webs are so interconnected (with closely spaced point bonds) that in tensile (elongation) the fibers at the polymer level are forced to stretch this results in polymer chains within the fiber permanently rearranging and as a result the fibers themselves potentially remaining permanently elongated (permanently strained) and no longer able to recover to their initial state.

In some configurations, the polymer fibers in the upper nonwoven layer and the polymer fibers of the lower nonwoven layer may be different. In some configurations, the polymer fibers of the upper nonwoven layer and the polymer fibers of the lower nonwoven layer may be the same.

Suitable nonwoven materials examples include, but are not limited to, the following materials: (i) a 40 gsm carded resilient nonwoven material produced by Yanjan China (material code; ATB Z87G-40-90) which is a carded nonwoven composed of a blend of 60% 2 DTex and 40% 4 DTex BiCo (PE/PET) fibers. The fibers are bonded (ATB=Through 'hot' Air Bonded) to create a wet resilient network. The material basis weight is 40 gsm and its caliper (under 7 KPa) is about 0.9 mm Without being limited by theory, it is believed that because of the presence of the 4 DTex BiCo fibers and the fiber-to-fiber bonded BiCo network, the material has a low Permanent Strain (less than about 0.013 mm/mm) and a sufficient Dry Recovery Energy (greater than about N*mm) in the Wet and Dry CD Ultra Sensitive 3 Point Bending Method; (ii) a 55 gsm resilient spunlace material produced by Sandler Germany (material code: 53FC041001), which is a hydro-entangled nonwoven that is produced via a carding step (like the nonwoven described above) followed by hydro-entangling with an elevated drying step (as described in U.S. Patent Publication No. 2020/0315873A1) that creates both an entangled and BiCo bonded resilient network. It comprises a fiber blend of 30% 10 DTex HS-PET, 50% 2.2 DTex BiCo (PE/PET), and 20% 1.3 DTex rayon. As such the material has a low Permanent Strain (less than about 0.013 mm/mm) and a sufficient Dry Recovery Energy (greater than about 0.03 N*mm) in the Wet and Dry CD Ultra Sensitive 3 Point Bending Method; and (iii) a 50 gsm resilient spunlace material produced by Sandler Germany (material code: 53FC041005 opt82), which is a hydro-entangled nonwoven that is produced via a carding step (like the nonwoven described above) followed by hydro-entangling with an elevated drying step (as described in U.S. Patent Publication No. 2020/0315873A1) that creates both an entangled and BiCo bonded resilient network. It comprises a fiber blend of 60% 5.8 DTex BiCo (PE/PET), 20% 3.3 DTex tri-lobal 'structural' rayon, and 20% 1.3 DTex rayon. As such the material has a low Permanent Strain (less than about 0.013 mm/mm) and a sufficient Dry Recovery Energy (greater than about 0.03 N*mm) in the Wet and Dry CD Ultra Sensitive 3 Point Bending Method. While this material has 40% rayon that can soften when wet, the use of structural tri-lobal rayon fibers helps structural stability in the wet state.

In combination with adjustment of pore size, volume, and number via selection of appropriate fiber size, basis weight, and extent of consolidation, the manufacturer may wish to select fiber constituents for having particular surface chemistry(ies), e.g., fibers with hydrophobic surfaces, hydrophilic surfaces, or a blend of differing fibers and/or z-direction stratification or gradient thereof. Fibers having hydrophilic surfaces will tend to attract and move aqueous components of menstrual fluid there along in a manner conducive to wicking and rapid fluid acquisition following discharge. At the same time, however, a predominance of hydrophilic fibers surfaces within the topsheet may increase a tendency of the topsheet to reacquire fluid from absorbent components beneath (rewet), which can cause an undesirable wet feel for the user. On the other hand, fibers having hydrophobic surfaces will tend to repel aqueous components of menstrual fluid and/or resist movement of fluid along their surfaces, thereby tending to resist wicking—but also to resist rewetting. The manufacturer may wish to seek an appropriate balance in selecting constituent fibers having hydrophilic surfaces, fibers having hydrophobic surfaces, or a blend and/or z-direction stratification thereof, in combination with fiber size, fiber consolidation level, and resulting topsheet pore size, volume and number, for any particular product design.

The inner core layer is produced in an airlaying process. Streams of cellulose fiber and AGM are carried on a fast moving airstream and deposited into a three dimensionally shaped pocket on a rotating forming drum with a vacuum below to draw the cellulose and AGM into the pocket in a laydown station. This shaped pocket provides the actual physical shape of the absorbent core structure. The upper or lower nonwoven may be first introduced onto the forming drum and under the vacuum the upper or lower nonwoven are drawn into the 3-dimensional pocket shape. In this case, the cellulose and AGM material stream is deposited on the upper (or lower nonwoven material) directly in the forming station. Prior to entering the forming station, the nonwoven is coated with an adhesive to provide a stronger connection of the cellulose and AGM to the nonwoven layer. On exiting the laydown section, the second remaining nonwoven layer is combined with the nonwoven carrying the cellulose and AGM layer exiting the laydown section. This second remaining nonwoven (either upper or lower nonwoven depending on what nonwoven is run through the laydown section) is precoated with adhesive to enable a perimeter seal and to better integrate the cellulose and AGM without hindering the flow of liquid into the cellulose and AGM matrix. In another approach, a nonwoven is not first introduced into the forming station and the cellulose and AGM mass is held on the forming drum under vacuum until it is ejected onto either the upper or lower nonwoven layer that has an adhesive applied as detailed above and then sealed with the second remaining nonwoven to create the absorbent core structure. The width of the upper and lower nonwoven webs are typically chosen to be wider than the maximum width of the shaped cellulose and AGM matrix so as to enable an effective perimeter seal where the two nonwovens connect, at least on the left and right most sides of the absorbent core structure.

The inner core layer may comprise any of a wide variety of liquid-absorbent materials commonly used in absorbent articles, such as comminuted wood pulp, which is generally referred to as airfelt. One suitable absorbent core material is an airfelt material which is available from Weyerhaeuser Company, Washington, USA, under Code No. FR516. Examples of other suitable liquid-absorbent materials for use in the absorbent core may include creped cellulose wadding; meltblown polymers including coform: chemically stiffened, modified or cross-linked cellulosic fibers; synthetic fibers such as crimped polyester fibers; peat moss; cotton, bamboo; absorbent polymer materials; or any equivalent, material or combinations of materials, or mixtures of these.

Absorbent polymer materials for use in absorbent articles typically comprise water-insoluble, water-swellable, hydrogel-forming crosslinked absorbent polymers which are capable of absorbing large quantities of liquids and of retaining such absorbed liquids under moderate pressure.

The absorbent polymer material for the absorbent cores according to the present disclosure may comprise superabsorbent particles, also known as "superabsorbent materials" or as "absorbent gelling materials". Absorbent polymer materials, typically in particle form, may be selected among polyacrylates and polyacrylate based materials, such as for example partially neutralized, crosslinked polyacrylates. The term "particles" refers to granules, fibers, flakes, spheres, powders, platelets and other shapes and forms known to persons skilled in the art of superabsorbent particles. In some aspects, the superabsorbent particles may be in the shape of fibers, i.e., elongated, acicular superabsorbent particles.

In some configurations, the inner core layer may comprise cellulosic fibers and superabsorbent particles. The inner core layer may comprise from about 50% to about 85% cellulosic fibers, or from about 55% to about 80%, or from about 60% to about 75%, all by weight of the inner core layer. The inner core layer may comprise from about 10% to about 50% superabsorbent particles, or from about 15% to about 50%, or from about 20% to about 40%, or from about 25% to about 35%, all by weight of the inner core layer. Preferably, the inner core layer may comprise from about 125 gsm to about 400 gsm cellulosic fibers.

In some configurations, the inner core layer may comprise from about 50% to about 85% cellulosic fibers and from about 15% to about 50% superabsorbent particles. The resulting absorbent core structure may have an average density of between about 0.045 g/cm$^3$ and about 0.15 g/cm$^3$, and/or between 0.045 g/cm$^3$ and 0.12 g/cm$^3$. The absorbent article may have an average density of between about 0.045 g/cm$^3$ and about 0.16 g/cm$^3$.

The absorbent core structures may compress and recover their original shape following the compression step. Suitable absorbent core structures require a low force to compress (less resistance) and the structure is able to recover its shape as the user, in a cyclic fashion, compresses and releases the compressive force with various body movements. To achieve this, the structure sustains sufficient recovery energy following multiple cyclic compressions. Without sufficient recovery energy the structure remains in a compressed bunched state with insufficient force (stored energy) to recover.

As shown in FIGS. 1, 2A-2C, 4, and 5 the absorbent core structure may comprise a plurality of structural bond sites 15. The structural bond sites 15 may be symmetric and/or asymmetrical and may be any shape including, but not limited to, circles, ovals, hearts, diamonds, triangles, squares, stars, and/or X shaped. The structural bond sites 15 may be on the absorbent article and/or on the absorbent core structure. In some configurations, the structural bond sites may have a bond area of from about 2 mm$^2$ to about 5 mm$^2$. In some configurations, the total structural bond area may be from about 0.5% to about 5%, or from about 0.75% to about 4.5%, or from about 1% to about 4% of the absorbent core structure, as measured according to the Structural Bond Sites Pattern Spacing and Area Measurement Method. In some configurations, the total structural bond area may be from about 1% to about 4% of absorbent article as measured according to the Structural Bond Sites Pattern Spacing and Area Measurement Method. The average distance between the structural bond sites may be from about 10 mm to about 32 mm. In some configurations, the average distance between the structural bond sites may be greater than about 20 mm. In some configurations, the structural bond sites may have a maximum width of from about 1 mm to about 6 mm, or from about 1.5 mm to about 5 mm, or from about 2 mm to about 4 mm Without being limited by theory, it is believed that the average distance between structural bond sites and/or the size of the structural bond sites may help to maintain the structural integrity of the absorbent core structure without creating an undesirable stiffness that may inhibit the ability of the absorbent article to conform to the body.

In some configurations, the structural bond sites may be distributed across the absorbent article and/or absorbent core structure or they may be clustered in regions of the absorbent article and/or absorbent core structure. In some configurations, the structural bond sites may be clustered in the middle region 22 of the absorbent article and/or absorbent core structure. In some configurations, the middle region 22 of the absorbent article and/or absorbent core structure may be free from structural bond sites and may be surrounded by an area of structural bond sites and/or embossing. In some configurations, the absorbent article may comprise one or more flex bond channel regions 160, wherein the flex bond channel regions may be a continuous depression and/or a series of individually compressed, closely spaced embossments.

In some configurations, the structural bond sites 15 may join the topsheet 110, the upper nonwoven layer 210, the absorbent core structure 10, and the lower nonwoven layer 220. In some configurations, the structural bond sites 15 may join the upper nonwoven layer 210, the absorbent core structure 10, and the lower nonwoven layer 220.

Suitable absorbent articles and/or absorbent core structures may comprise an upper nonwoven layer and lower nonwoven layer that are closer together in the Z direction at the structural bond sites but are not melted together. Since these structural bond sites are not melted together, they may not be permanent in nature and rather may intermingle the materials within the structural bond site. In some configurations, the structural bond sites may be substantially free of fusion bonds.

While the shape of the structural bond sites can be any shape, suitable shapes may be more detailed shapes such as asymmetrical shapes (versus simple dots).

The absorbent article 20 may be resilient and conformable and may deliver a superior in-use experience without substantially bunching and/or compressing. The absorbent article may be exposed to bodily forces and may recover to its original state. The absorbent article may have a CD Dry Modulus of between about 0.07 and 0.30 N/mm$^2$ as measured in the Wet and Dry CD and MD 3 Point Bend Method, or from about 0.10 to about 0.25 N/mm$^2$, or from about 0.10 to about 0.20 N/mm$^2$.

The absorbent article may have a of Dry Caliper between about 2.0 mm and about 6.0 mm, or from about 2.0 mm and about 4.5 mm, or from about 2.5 mm to about 4.0 mm, or from about 2.75 mm to about 3.5 mm, as measured according to the Wet and Dry CD and MD 3-Point Method. In some configurations, the absorbent article may have a CD Dry Modulus of between about 0.07 and 0.30 N/mm$^2$ and a Dry Caliper between about 2.0 mm and about 4.5 mm as measured according to the Wet and Dry CD and MD 3-Point Method, or a CD Dry Modulus of between from about 0.10 to about 0.25 N/mm$^2$ and a Dry Caliper of from about 2.50 mm to about 4.0 mm, or a CD Dry Modulus of between about from about 0.10 to about 0.20 N/mm$^2$ and a Dry Caliper of from about 2.75 mm to about 3.5 mm. The absorbent article may have a CD Dry Bending Stiffness of between about 10.0 to about 30.0 N*mm$^2$ as measured in the Wet and Dry CD and MD 3 Point Bend Method, or about 10.0 and about 25.0 N*mm$^2$, or about 10 to about 20 N*mm$^2$, or about 13 to about 20 N*mm$^2$. Particularly suitable absorbent articles include those having a CD Dry Bending Stiffness of between about 10.0 and about 30.0 N*mm$^2$ and a Dry Caliper of from about 2.5 mm to about 4.0 mm as measured according to the Wet and Dry CD and MD 3-Point Method, or a CD Dry Bending Stiffness of about 10 to about 25 N*mm$^2$ and a Dry Caliper of between about 2.5 and 4.0 mm, or a CD Dry Bending Stiffness about 13 to about 30 N*mm$^2$ and a Dry Caliper of from about 2.75 mm to about 3.5 mm.

The absorbent article may have a 5$^{th}$ Cycle Wet Energy of Recovery of from about 1.0 to 3.5 N*mm, or about 1.5 to about 3.0 N*mm, or about 1.5 to about 2.8 N*mm Particularly suitable absorbent articles may have a 5$^{th}$ Cycle Wet Energy of Recovery of between about 1.0 and 3.5 N*mm and a 5$^{th}$ Cycle Wet % Recovery of from about 29% to about 40%, or a 5$^{th}$ Cycle Wet Energy of Recovery of from about 1.5 to about 3.0 N*mm and a 5$^{th}$ Cycle Wet % Recovery of from about 29% to about 40%, or a 5$^{th}$ Cycle Wet Energy of Recovery from about 1.5 to about 2.75 N*mm and a 5$^{th}$ Cycle Wet % Recovery of from about 29% to about 40%.

Absorbent articles comprising the absorbent core structures as disclosed herein may also need to deliver a dry touch to the consumer following the addition of fluid as measured by the light touch rewet method. Absorbent core structures and absorbent articles meeting the above characteristics are designed to comfortably and gently conform more closely and more completely to the wearer's complex anatomical genital shape. Such absorbent articles therefore may also need to be dry to the touch following discharge so as not to irritate the sensitive genital tissues. As such absorbent articles described herein may also maintain a Light Touch Rewet value of less than about 0.15 grams, or less about 0.12 grams, or from about 0 to about 0.15 grams, or from about 0 to about 0.12 grams.

Figures 2B, 2C:
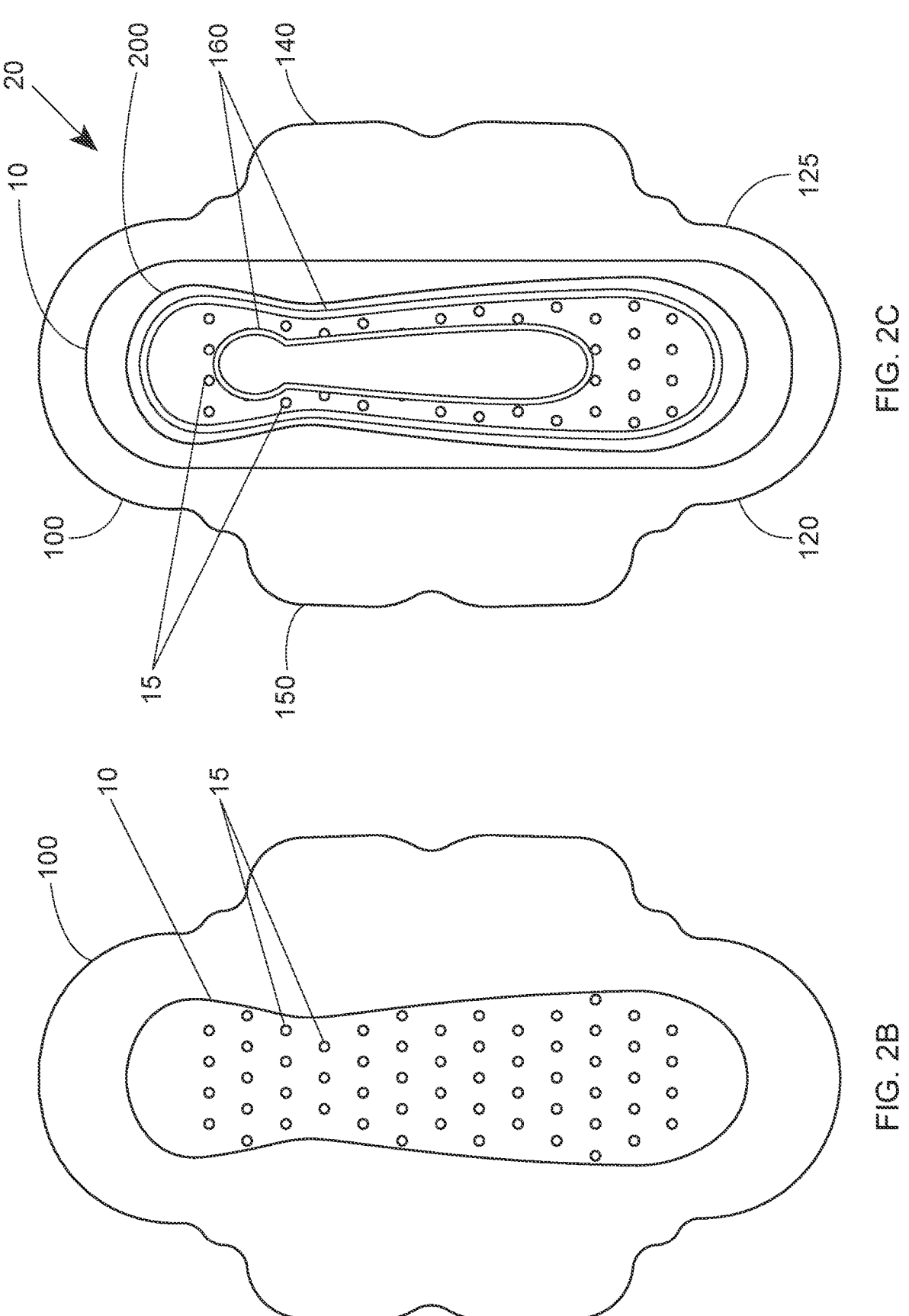
FIG. 2B is another representation of an absorbent article in accordance with the present disclosure.
FIG. 2C is another representation of an absorbent article in accordance with the present disclosure.

As shown in FIGS. 2A-2C, the absorbent article 20 further comprises a chassis 100 comprising an absorbent core structure 10. As shown, the absorbent core structure 10 and/or the inner core layer 200 may comprise a generally hourglass shape. However, any suitable shape may be utilized. Some examples include offset hourglass (one end is wider than an opposite end and a narrowed mid-section between the ends), bicycle seat shape (one end and central portion are narrower than second end), etc. Side edges 120 and 125 may follow the general contour of the absorbent core structure. So where, the absorbent core structure has an hourglass shape the side edges of the absorbent article 120, 125 may be arranged in an hourglass shape as well. However, forms are contemplated where the side edges 120 and 125 are generally straight or slightly curved such that they do not follow the contour of the absorbent core structure. Additional details are discussed hereafter. The absorbent article 20 may be symmetric about the longitudinal centerline or asymmetric about the longitudinal centerline 80. Similarly, the absorbent article 20 may be symmetric about the lateral centerline 90 or asymmetric about the lateral centerline 90.

Topsheet

Figure 6:
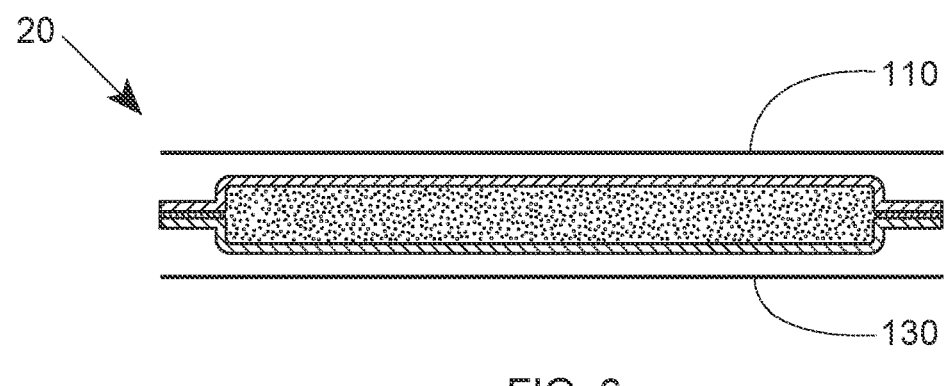
FIG. 6 is a cross section of an absorbent article in accordance with the present disclosure.

Topsheet 110 may be formed of any suitable nonwoven web or formed film material (see FIG. 6). Referring back to the figures, the topsheet 110 is positioned adjacent a wearer-facing surface of the absorbent article 20 and may be joined thereto and to the backsheet 130 by any suitable attachment or bonding method. The topsheet 110 and the backsheet 130 may be joined directly to each other in the peripheral regions outside the perimeter of the absorbent core structure and may be indirectly joined by directly joining them respectively to wearer-facing and outward-facing surfaces of the absorbent article or additional optional layers included with the absorbent article.

The absorbent article 20 may have any known or otherwise effective topsheet 110, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. Some suitable examples of topsheet materials include films, nonwovens, laminate structures including film/nonwoven layers, film/film layers, and nonwoven/nonwoven layers.

Nonlimiting examples of nonwoven web materials that may be suitable for use to form the topsheet 110 include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

The topsheet 110 may be compliant, soft feeling, and non-irritating to the wearer's skin. Further, the topsheet 110 may be liquid pervious permitting liquids (e.g., urine, menses) to readily penetrate through its thickness. Some suitable examples of topsheet materials include films, nonwovens, laminate structures including film/nonwoven layers, film/film layers, and nonwoven/nonwoven layers. Other exemplary topsheet materials and designs are disclosed in U.S. Patent Application Publication Nos. 2016/0129661, 2016/0167334, and 2016/0278986.

In some examples, the topsheet 110 may include tufts as described in U.S. Pat. Nos. 8,728,049; 7,553,532; 7,172, 801; 8,440,286; 7,648,752; and 7,410,683. The topsheet 20 may have a pattern of discrete hair-like fibrils as described in U.S. Pat. No. 7,655,176 or U.S. Pat. No. 7,402,723. Additional examples of suitable topsheet materials include those described in U.S. Pat. Nos. 8,614,365; 8,704,036; 6,025,535; and US Patent Publication No. 2015/041640. Another suitable topsheet may be formed from a three-dimensional substrate as detailed in US 2017/0258647. The topsheet may have one or more layers, as described in US Patent Publication Nos. 2016/0167334; US 2016/0166443; and US 2017/0258651.

In some examples a topsheet 110 may be formed of a nonwoven web material of a spunbond web including single-component continuous fibers, or alternatively, bi-component or multi-component fibers, or a blend of single-component fibers spun of differing polymer resins, or any combination thereof. The topsheet may also be a formed nonwoven topsheet as disclosed in US Patent Publication No. 2019/0380887.

In order to ensure that fluid contacting the top (wearer-facing) surface of a topsheet will move suitably rapidly in a z-direction to the bottom (outward-facing) surface of the topsheet where it can be drawn into the absorbent article, it may be important to ensure that the nonwoven web material forming the topsheet has an appropriate weight/volume density, reflecting suitable presence of interstitial passage-ways (sometimes known as "pores") among and between the constituent fibers, through which fluid may move within the nonwoven material. In some circumstances a nonwoven material with fibers that are consolidated too densely may have insufficient numbers and/or volumes and/or sizes of pores, and the nonwoven will obstruct rather than facilitate rapid downward z-direction fluid movement. On the other hand, a nonwoven with fibers that are too large and/or not consolidated enough to provide a certain level of opacity (for purposes of concealing absorbed fluid in the layers beneath) and a substantial appearance may be negatively perceived by users.

The caliper of the topsheet material may be controlled, to balance competing needs for opacity and loft (which call for a higher caliper) vs. a limitation on the z-direction distance that discharged fluid travels through the topsheet from the wearer-facing surface to the outward-facing surface, to reach the absorbent core components below. Thus, it may be desired that the manufacture of the topsheet material be controlled to produce a topsheet material having a caliper of from about 0.20 mm to about 1.0 mm, or from about 0.25 mm to about 0.80 mm, or from about 0.30 mm to about 0.60 mm.

Secondary Topsheet (STS)

An STS layer may be included, in some circumstances, between the topsheet and the absorbent core structure to enable the absorbent core structure to readily receive a sudden discharge of fluid, and after receipt, to wick it along x- and y-directions to distribute it across the underlying absorbent core structure.

If included, an STS may be a nonwoven fibrous structure which may include cellulosic fibers, non-cellulosic fibers (e.g., fibers spun from polymer resin(s)), or a blend thereof. To accommodate the folding and lateral gathering of the absorbent article 20, and of the absorbent core structure 10, as described herein, the STS may be formed of a material that is relatively pliable (i.e., has relatively low bending stiffness).

A number of particular examples of suitable STS compositions and structures, as well as combinations thereof with suitable topsheet compositions and structures, are further described in U.S. applications. Ser. Nos. 16/831,862; 16/831,854; 16/832,270; 16/831,865; 16/831,868; 16/831,870; and Ser. No. 16/831,879; and U.S. Provisional Apps. Ser. Nos. 63/086,610 and 63/086,701. Additional suitable examples are described in U.S. Pat. No. 9,504,613; WO 2012/040315; and US 2019/0021917.

In some configurations, the absorbent article may be free of a secondary topsheet.

Backsheet

The backsheet 130 may be positioned beneath or subjacent an outward-facing surface of the absorbent core structure 10 and may be joined thereto by any suitable attachment methods. For example, the backsheet 130 may be secured to the absorbent core structure 10 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent core structure 10 is not joined directly to the backsheet 130.

The backsheet 130 may be impermeable or substantially impermeable by aqueous liquids (e.g., urine, menstrual fluid) and may be manufactured from a thin plastic film, although other flexible liquid impermeable materials may also be used. As used herein, the term "flexible" refers to materials which are compliant and will readily conform to the general shape and contours of the human body. The backsheet 130 may prevent, or at least substantially inhibit, fluids absorbed and contained within the absorbent core structure 10 from escaping and reaching articles of the wearer's clothing which may contact the absorbent article 20, such as underpants and outer clothing. However, in some instances, the backsheet 130 may be made and/or adapted to permit vapor to escape from the absorbent core structure 10 (i.e., the backsheet is made to be breathable), while in other instances the backsheet 130 may be made so as not to permit vapors to escape (i.e., it is made to be non-breathable). Thus, the backsheet 130 may comprise a polymeric film such as thermoplastic films of polyethylene or polypropylene. A suitable material for the backsheet 130 is a thermoplastic film having a thickness of from about 0.012 mm (0.5 mil) to about 0.051 mm (2.0 mils), for example. Any suitable backsheet known in the art may be utilized with the present invention.

Some suitable examples of materials suitable for forming a backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523; 3,989,867; 3,156,242; WO 97/24097; U.S. Pat. Nos. 6,623,464; 6,664,439; and 6,436, 508.

The backsheet 130 may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat.

Nos. 3,881,489; 4,341,216; 4,713,068; 4,818,600; EP 203 821; EP 710 471; EP 710 472; and EP 0 793 952.

Other Features

In some configurations, the absorbent article 20 may be provided with adhesive deposits to provide a mechanism for the user to adhere the absorbent article to the inside of her underpants in the crotch region thereof. When the absorbent article 20 is packaged for shipping, handling and storage prior to use, adhesive deposits may be covered by one or more sheets of release film or paper (not shown) that covers/shields the adhesive deposits from contact with other surfaces until the user is ready to remove the release film or paper and place the absorbent article in her underpants for wear/use.

In some configurations, the absorbent article 20 may include opposing wing portions 140, 150 on each side, extending laterally beyond longitudinal edges of the absorbent portions of the absorbent article by a comparatively greater width dimension than that of the forward and rearward portions of the absorbent article. Wings are currently commonly provided with feminine hygiene absorbent articles. As provided, they typically have deposits of adhesive applied to their outward-facing surfaces (surface are outward-facing prior to placement of the absorbent article within the user's underwear and application of the wings). The wing portions may also include deposits of adhesive as described above, which enable the user to wrap the wing portions through the leg openings of the underpants and around the inside edges thereof, and adhere the wing portions to the outward-facing surface/underside of the underpants in the crotch region, providing supplemental holding support for the absorbent article and helping guard the underpants proximate the leg edges thereof against soiling.

Test Methods

Layers of Interest

For any of the methods below in which all the component layers of an article will not be tested, the layers of interest may be separated using cryo-spray as needed from layers which will not be tested.

Strain to Break Method

The force versus displacement behavior of a sample is measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The sample is subjected to tensile elongation at a constant rate (mm/sec) until it breaks, and the percent strain to break is measured. All testing is performed in a room controlled at 23° C.±3 C° and 50%±2% relative humidity and test samples are conditioned in this environment for at least 2 hours prior to testing.

The fixtures used to grip the test specimen are lightweight (<80 grams), vise action clamps with half cylinder steel versus rubber coated steel grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any folds or wrinkles. The test specimen is 100 mm long (parallel to the lateral axis, or intended lateral axis of the article) and 25.4 mm wide (parallel to the longitudinal axis, or intended longitudinal axis of the article). In like fashion, five replicate test specimens are prepared.

Prepare the universal test frame as follows. Set the initial grip to grip separation distance to a nominal gage length of 80 mm, then zero the crosshead. Program the test frame to move the grips closer together by an intentional slack of 1 mm to ensure no pretension force exists on the test specimen at the onset of the test. (During this motion, the specimen will become slack between the grips.) Next, the grips will move apart at a slack speed of 1 mm/s until the slack preload of 0.05 N is exceeded. (At this point, the crosshead position signal is used to compute the sample slack, the adjusted gage length, and the strain is defined at zero, 0.0). The grips will then move apart at a speed of 1 mm/s until the sample breaks or the extension limit of the instrument is exceeded.

The test is executed by inserting the test specimen into the grips such that the long axis of the specimen is parallel and centered with the motion of the crosshead. Start the test and continuously collect force ("load") and displacement data at a data acquisition rate of 100 Hz.

Construct a graph of load (N) versus displacement (mm). Determine the peak load from the curve, then determine the break sensitivity as follows. Determine the crosshead position at which the load signal decreases by 75% after the peak load is reached, and record as specimen final length (Lf) to the nearest 0.01 mm. The initial length of the specimen is defined by the crosshead position when the slack preload of 0.05 N is exceeded, and this value is recorded as specimen initial length (Li) to the nearest 0.01 mm Calculate the percent strain to break as follows, and record to the nearest 1 percent.

$$\% \text{ Strain to Break} = ((Lf-Li)/Li)*100$$

In like fashion, the procedure is repeated for all five replicate test specimens. The arithmetic mean of % strain to break among the five replicate test specimens is calculated and reported as % Strain to Break to the nearest 1 percent.

Wet and Dry CD and MD 3 Point Bend Method

The bending properties of an absorbent article test sample are measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The bottom stationary fixture consists of two cylindrical bars 3.175 mm in diameter by 110 mm in length, made of polished stainless steel each mounted on each end with frictionless roller bearings. These 2 bars are mounted horizontally, aligned front to back and parallel to each other, with top radii of the bars vertically aligned and are free to rotate around the diameter of the cylinder by the frictionless bearings. Furthermore, the fixture allows for the two bars to be moved horizontally away from each other on a track so that a gap can be set between them while maintaining their orientation. The top fixture consists of a third cylinder bar also 3.175 mm in diameter by 110 mm in length, made of polished stainless steel mounted on each end with frictionless roller bearings. When in place the bar of the top fixture is parallel to and aligned front to back with the bars of the bottom fixture and is centered between the bars if the bottom fixture. Both fixtures include an integral adapter appropriate to fit the respective position on the universal test frame and lock into position such that the bars are orthogonal to the motion of the crossbeam of the test frame.

Set the gap ("Span") between the bars of the lower fixture to 25 mm±0.5 mm (center of bar to center of bar) with the upper bar centered at the midpoint between the lower bars. Set the gage (bottom of top bar to top of lower bars) to 1.0 cm.

The thickness ("caliper") of the test specimen is measured using a manually-operated micrometer equipped with a pressure foot capable of exerting a steady pressure of 0.1 psi±0.01 psi. The manually-operated micrometer is a dead-weight type instrument with readings accurate to 0.01 mm A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as caliper to the nearest 0.01 mm.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

The absorbent article samples are conditioned at 23° C.±3° C. and 50%±2% relative humidity two hours prior to testing. Dry test specimens are taken from an area of the sample that is free from any seams and residua of folds or wrinkles, and ideally from the center of absorbent article (intersection of longitudinal and lateral midlines). The dry specimens are prepared for MD (machine direction) bending by cutting them to a width of 50.8 mm along the CD (cross direction; parallel to the lateral axis of the sample) and a length of 50.8 mm along the MD (parallel to the longitudinal axis of the sample), maintaining their orientation after they are cut, and marking the body-facing surface (or the surface intended to face the body of a finished article). The dry specimens are prepared for CD (machine direction) bending by cutting them to a width of 50.8 mm along the MD (cross direction; parallel to the lateral axis of the sample) and a length of 50.8 mm along the CD (parallel to the longitudinal axis of the sample), maintaining their orientation after they are cut, and marking the body-facing surface (or the surface intended to face the body of a finished article). Measure the thickness of the test specimen, as described herein, and record as dry specimen caliper to the nearest 0.01 mm Now measure the mass of the test specimen and record as dry mass to the nearest 0.001 grams. Calculate the basis weight of the specimen by dividing the mass (g) by the area (0.002581 m²) and record as dry specimen basis weight to the nearest 0.01 g/m². Calculate the bulk density of the specimen by dividing the specimen basis weight (g/m²) by the specimen thickness (mm), then dividing the quotient by 1000, and record as dry specimen density to the nearest 0.01 g/cm³. In like fashion, five replicate dry test specimens are prepared.

Wet test specimens are initially prepared in the exact manner as for the dry test specimen, followed by the addition of test fluid just prior to testing, as follows. First, the thickness and mass of the dry specimen is measured, as described herein, and recorded as initial thickness to the nearest 0.01 mm and initial mass to the nearest 0.001 g. Next, the dry specimen is fully submersed in the test fluid for 60 seconds. After 60 seconds elapse, the specimen is removed from the test fluid and oriented vertically for 30 seconds to allow any excess fluid to drip off. Now the thickness and mass of the wet specimen are measured, as described herein, and recorded as wet specimen caliper to the nearest 0.01 mm and wet specimen mass to the nearest 0.001 g. If desired, the mass of test fluid in the test specimen is calculated by subtracting the initial mass (g) from the wet specimen mass (g) and recording as test specimen fluid amount to the nearest 0.001 g. After the wet test specimen is removed from the test fluid, it must be tested within 10 minutes. In like fashion, five replicate wet test specimens are prepared.

Program the universal test frame for a flexural bend test, to move the crosshead such that the top fixture moves down with respect to the lower fixture at a rate of 1.0 mm/sec until the upper bar touches the top surface of the specimen with a nominal force of 0.02 N, then continue for an additional 12 mm. The crosshead is then immediately returned to the original gage at a rate of 1.0 mm/s. Force (N) and displacement (mm) data are continuously collected at 100 Hz throughout the test.

Load a dry test specimen such that it spans the two lower bars and is centered under the upper bar, with its sides parallel to the bars. For MD bending, the MD direction of the test specimen is perpendicular to the length of the 3 bars. Start the test and continuously collect force and displacement data.

Construct a graph of force (N) versus displacement (mm). From the graph, determine the maximum peak force and record as dry MD peak load to the nearest 0.01 N. Now calculate the maximum slope of the curve between initial force and maximum force (during the loading portion of the curve) and record to the nearest 0.1 unit. Calculate the modulus as follows, and record as dry MD modulus to the nearest 0.001 $N/mm^2$.

> CD or MD Dry or Wet Bending Modulus $(N/mm^2)$=
> (Slope$\times$(Span$^3$))/(4$\times$specimen width$\times$(specimen caliper$^3$))

Calculate bending stiffness as follows, and record as dry MD bending stiffness to the nearest 0.1 N mm$^2$.

> CD or MD Dry or Wet Bending Stiffness ($N$ mm$^2$)
> =Modulus$\times$Moment of Inertia where Moment of
> Inertia (mm$^4$)=(specimen width$\times$(specimen caliper$^3$))/12

In like fashion, the procedure is repeated for all five replicates of the dry test specimens. The arithmetic mean among the five replicate dry test specimens is calculated for each of the parameters and reported as Dry Specimen 'Caliper' to the nearest 0.01 mm, Dry Specimen Basis Weight to the nearest 0.01 g/m$^2$, Dry Specimen Density to the nearest 0.001 g/cm$^3$, Dry CD or MD Peak Load to the nearest 0.01 N, Dry CD or MD Bending Modulus to the nearest 0.001 N/mm$^2$, and Dry CD or MD Bending Stiffness to the nearest N mm$^2$.

The overall procedure is now repeated for all five replicates of the wet test specimens, reporting results as Wet CD or MD Peak Load to the nearest 0.01 N, Wet CD or MD Bending Modulus to the nearest 0.001 N/mm$^2$, and Wet CD or MD Bending Stiffness to the nearest N mm$^2$.

Wet and Dry CD Ultra Sensitive 3 Point Bending Method

The CD (cross-direction) bending properties of a test sample are measured using an ultra sensitive 3 point bend test on a universal constant rate of extension test frame (a suitable instrument is the MTS Alliance using TestSuite Software, as available from MTS Systems Corp., Eden Prairie, MN, or equivalent) equipped with a load cell appropriate for the forces being measured. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The ultra sensitive 3 point bend method is designed to maximize the force signal to noise ratio when testing materials with very low bending forces. The force signal is maximized by using a high sensitivity load cell (e.g., 5N), using a small span (load is proportional to the span cubed) and using a wide specimen width (total measured load is directly proportional to width). The fixture is designed such that the bending measurement is performed in tension, allowing the fixture mass to be kept to a minimum. Noise in the force signal is minimized by holding the load cell stationary to reduce mechanical vibration and inertial effect and by making the mass of the fixture attached to the load cell as low as possible.

Figure 7A:
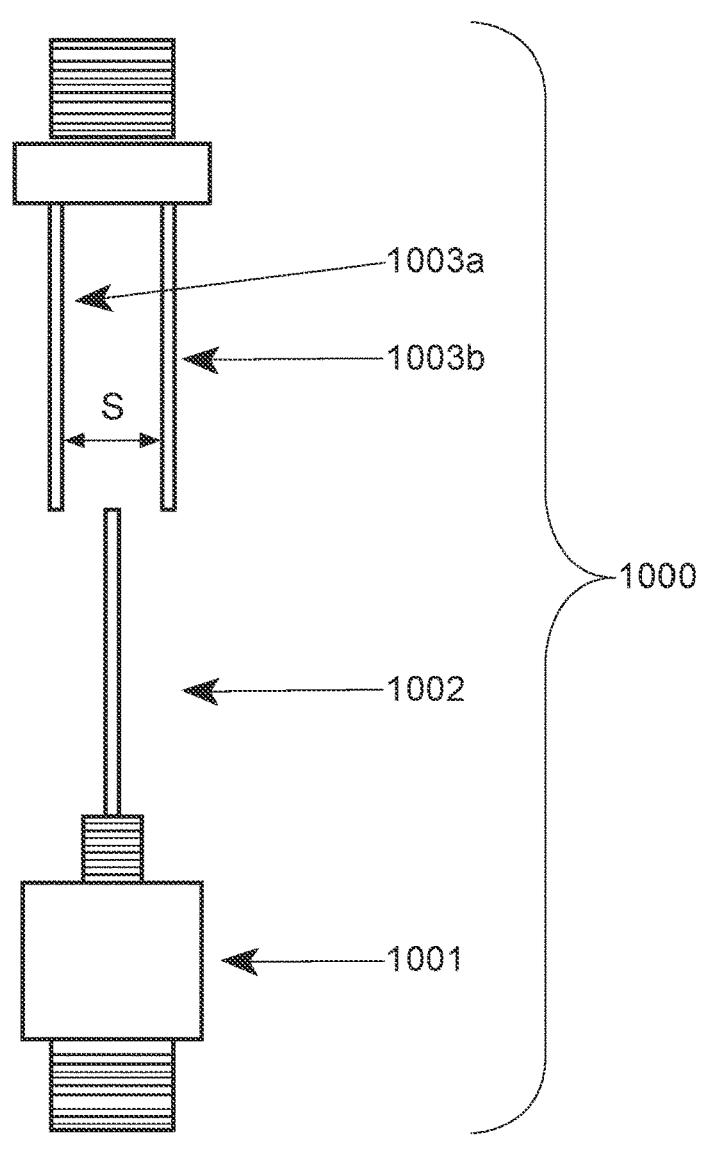
FIGS. 7A-C are a test method arrangement for the Wet and Dry CD Ultra Sensitive 3 Point Bending Method.
Figure 7B:
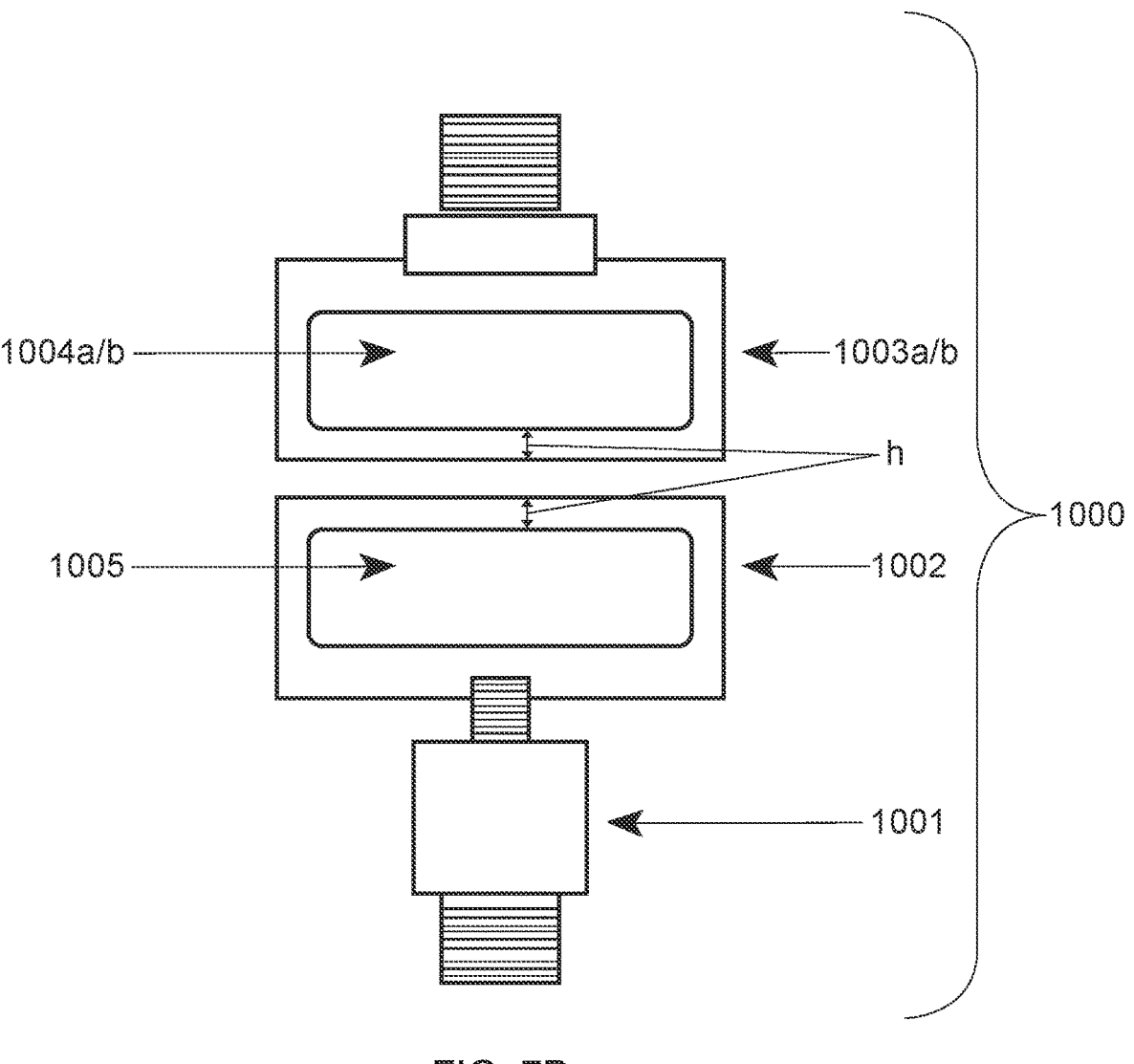
Figure 7C:
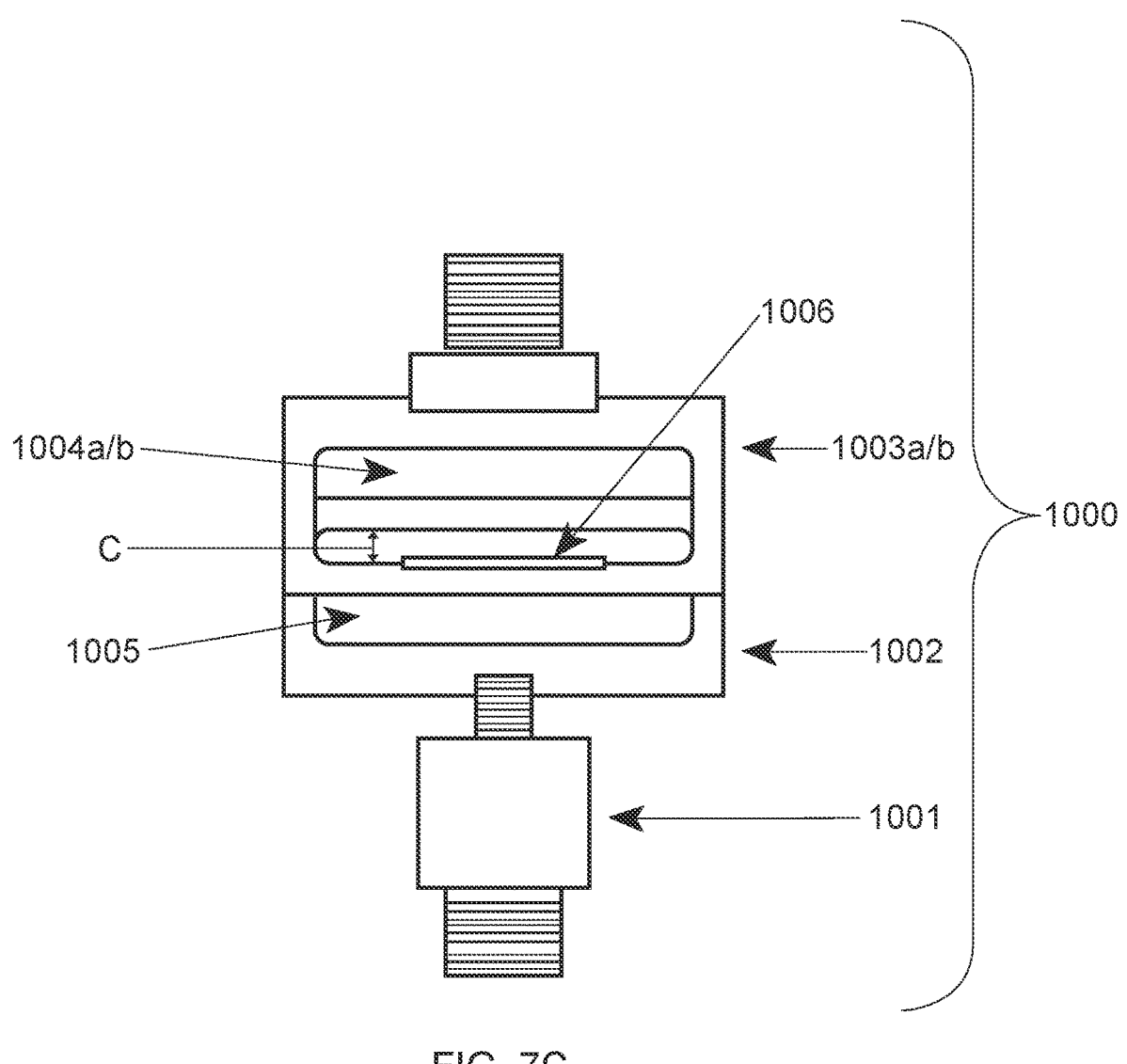

Referring to FIGS. 7A-7C, the load cell 1001 is mounted on the stationary crosshead of the universal test frame. The ultra sensitive fixture 1000 consists of three thin blades constructed of a lightweight, rigid material (such as aluminum, or equivalent). Each blade has a thickness of 1.0 mm, rounded edges and a length that is able to accommodate a bending width of 100 mm Each of the blades has a cavity 1004*a* and 1004*b* (outside blades) and 1005 (central blade) cut out to create a height, h, of 5 mm of blade material along their horizontal edges. The two outside blades 1003*a* and 1003*b* are mounted horizontally to the moveable crosshead of the universal test frame, aligned parallel to each other, with their horizontal edges vertically aligned. The span, s, between the two outside blades 1003*a* and 1003*b* is 5 mm±0.1 mm (inside edge to inside edge). The central blade 1002 is mounted to the load cell on the stationary crosshead of the universal test frame. When in place, the central blade 1002 is parallel to the two outside blades 1003*a* and 1003*b* and centered at the midpoint between the outside blades 1003*a* and 1003*b*. The blade fixtures include integral adapters appropriate to fit the respective positions on the universal test frame and lock into position such that the horizontal edges of the blades are orthogonal to the motion of the crossbeam of the universal test frame.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

Samples are conditioned at 23° C.±3° C. and 50%±2% relative humidity two hours prior to testing. Dry test specimens are taken from an area of the sample that is free from any seams and residua of folds or wrinkles. The dry specimens are prepared for CD bending (i.e., bending normal to the lateral axis of the sample) by cutting them to a width of 50.0 mm along the CD (cross direction; parallel to the lateral axis of the sample) and a length of 100.0 mm along the MD (machine direction; parallel to the longitudinal axis of the sample), maintaining their orientation after they are cut and marking the body-facing surface (or the surface intended to face the body of a finished article). In like fashion, five replicate dry test specimens are prepared.

Wet test specimens are initially prepared in the exact manner as for the dry test specimen, followed by the addition of test fluid just prior to testing, as follows. The dry specimen is fully submersed in the test fluid for 60 seconds. After 60 seconds elapse, the specimen is removed from the test fluid and oriented vertically for 30 seconds to allow any excess fluid to drip off. After the wet test specimen is removed from the test fluid, it must be tested within 10 minutes. In like fashion, five replicate wet test specimens are prepared.

The universal test frame is programmed such that the moveable crosshead is set to move in a direction opposite of the stationary crosshead at a rate of 1.0 mm/s. Crosshead movement begins with the specimen 1006 lying flat and undeflected on the outer blades 1003a and 1003b, continues with the inner horizontal edge of cavity 1005 in the central blade 1002 coming into contact with the top surface of the specimen 1006, and further continues for an additional 4 mm of crosshead movement. The crosshead stops at 4 mm and then immediately returns to zero at a speed of 1.0 mm/s. Force (N) and displacement (mm) are collected at 50 Hz throughout.

Prior to loading the test specimen 1006, the outside blades 1003a and 1003b are moved towards and then past central blade 1002 until there is approximately a 3 mm clearance, C, between the inner horizontal edges of cavities 1004a and 1004b in the outside blades 1003a and 1003b and the inner horizontal edge of cavity 1005 in the central blade 1002 (see FIG. 7C). The specimen 1006 is placed within clearance C such that it spans the inner horizontal edges of cavities 1004a and 1004b in the outside blades 1003a and 1003b, oriented such that the MD (short side) of the specimen is perpendicular to the horizontal edges of the blades and the body-facing surface of the specimen is facing up. Center the specimen 1006 between the outside blades 1003a and 1003b. Slowly move the outside blades 1003a and 1003b in a direction opposite of the stationary crosshead until the inner horizontal edge of cavity 1005 in the central blade 1002 touches the top surface of the specimen 1006. Start the test and continuously collect force and displacement data.

Force (N) is plotted versus displacement (mm). The maximum peak force is recorded to the nearest 0.001 N. The area under the curve from load onset up to the maximum peak force is calculated and recorded as bending energy to the nearest 0.001 N-mm. The recovery energy is calculated as the area under the curve where the force is unloaded from the maximum peak to 0.0 N and recorded as recovery energy to the nearest 0.001 N-mm. In like fashion, repeat the entire test sequence for a total of five dry test specimens and five wet test specimens.

For each test specimen type (dry and wet), the arithmetic mean of the maximum peak force among like specimens is calculated to the nearest 0.001 N and recorded as Dry Peak Load and Wet Peak load, respectively. For each test specimen type (dry and wet), the arithmetic mean of bending energy among like specimens is calculated to the nearest 0.001 N-mm and reported as Dry Bending Energy and Wet Bending Energy, respectively. For each test specimen type (dry and wet), the arithmetic mean of recovery energy among like specimens is calculated to the nearest 0.001 N-mm and reported as Dry Recovery Energy and Wet Recovery Energy, respectively.

Wet and Dry Bunched Compression Method

The bunched compression test method measures the force versus displacement behavior across five cycles of load application ("compression") and load removal ("recovery") of an absorbent article test sample that has been intentionally "bunched", using a universal constant rate of extension test frame (a suitable instrument is the MTS Alliance using TestSuite software, as available from MTS Systems Corp., Eden Prairie, MN, or equivalent) equipped with a load cell for which the forces measured are within 1% to 99% of the limit of the cell. The test is executed on dry test specimens as well as wet test specimens that are dosed with a specified amount of test fluid. The intention of this method is to mimic the deformation created in the z-plane of the crotch region of an absorbent article, or components thereof, as it is worn by the wearer during sit-stand movements. All testing is performed in a room controlled at 23° C.±3 C° and 50%±2% relative humidity.

Figure 8:
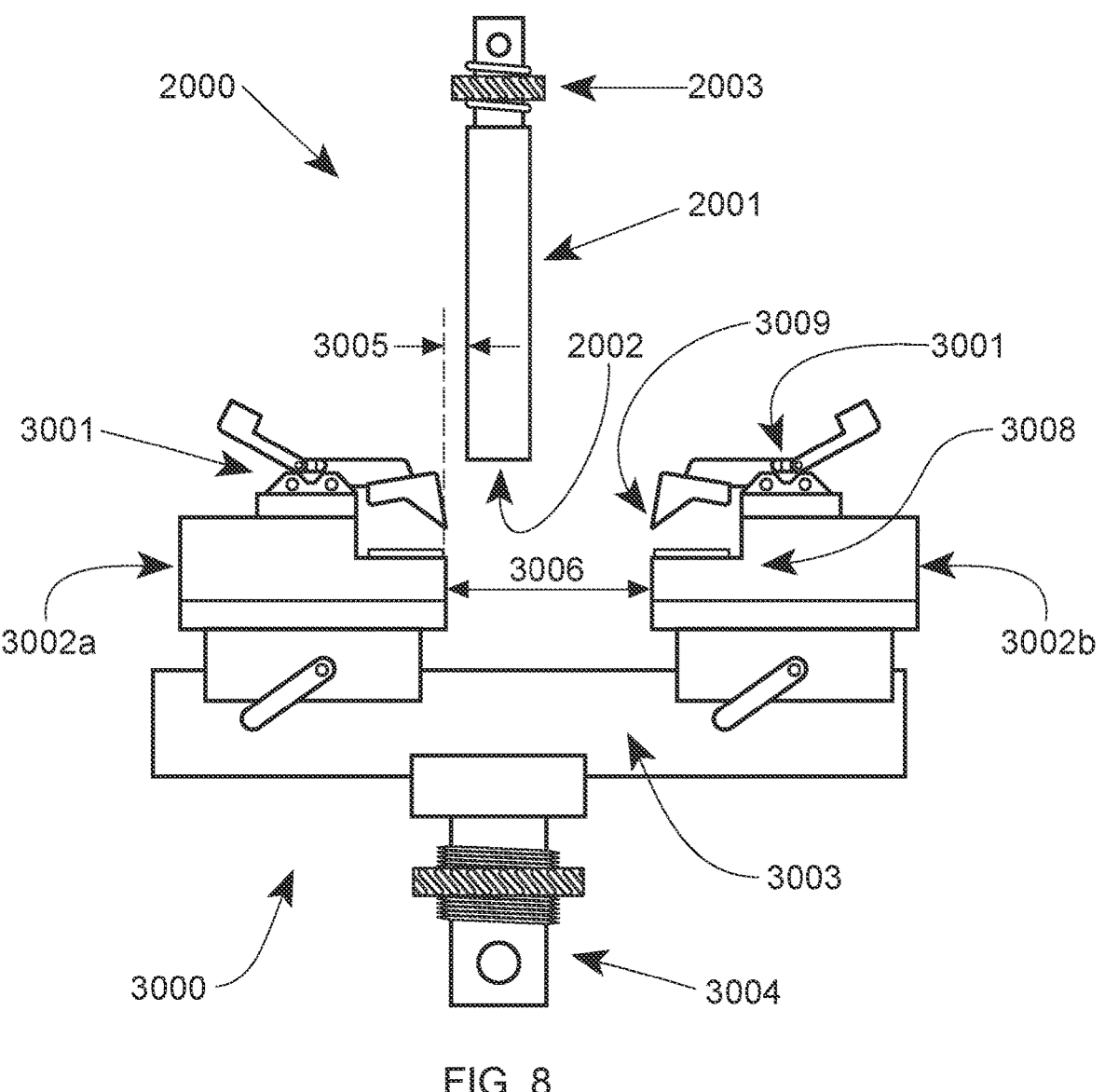
FIGS. 8, 9A and 9B are the test method arrangement for the Wet and Dry Bunched Compression Test.
Figure 9A:
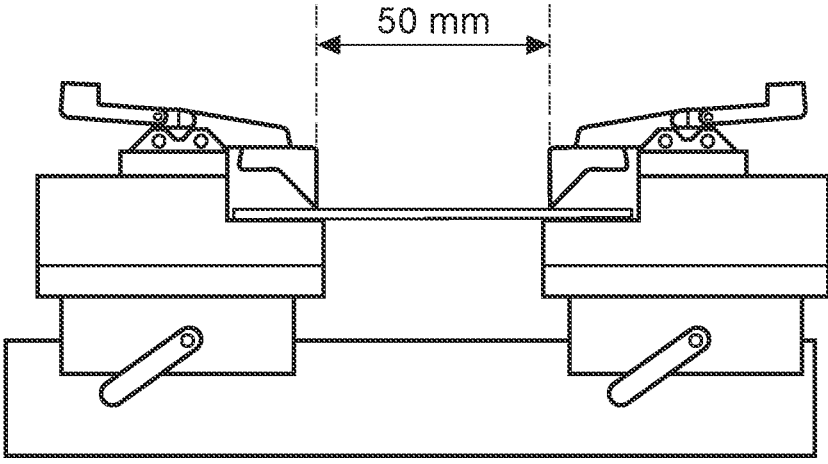
Figure 9B:
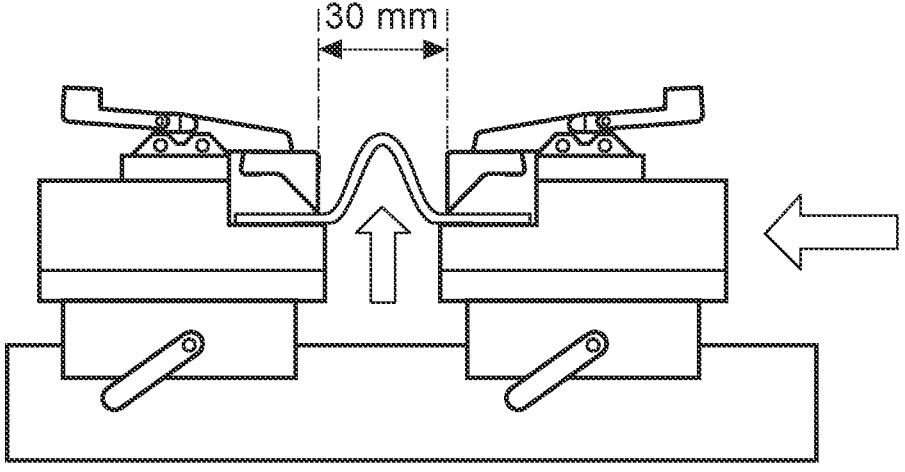

The test apparatus is depicted in FIGS. 8-9B. The bottom stationary fixture 3000 consists of two matching sample clamps 3001 each 100 mm wide, each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Test samples are conditioned at 23° C.±3 C° and 50%±2% relative humidity for at least 2 hours before testing. Prepare the test specimen as follows. When testing an intact absorbent article, remove the release paper from any panty fastening adhesive on the garment facing side of the article, if present. Lightly apply talc powder to the adhesive to mitigate any tackiness. If there are cuffs, excise them with scissors so as not to disturb the topsheet or any other underlying layers of the article. Place the article, body facing surface up, on a benchtop. On the article, mark the intersection of the longitudinal midline and the lateral midline. Using a rectangular cutting die or equivalent cutting means, cut a specimen 100 mm in the longitudinal direction by 80 mm in the lateral direction, centered at the intersection of the midlines. When testing a material layer or layered components from an absorbent article, place the material layer or layered components on a benchtop and orient as it would be integrated into a finished article, i.e., identify the body facing surface and the lateral and longitudinal axis. Using a rectangular cutting die, or equivalent cutting means, cut a specimen 100 mm in the longitudinal direction by 80 mm in the lateral direction, centered at the intersection of the midlines. Measure the mass of the specimen and record to the nearest 0.001 grams. Calculate the basis weight of the specimen by dividing the mass (g) by the area (0.008 $m^2$) and record as basis weight to the nearest 1 $g/m^2$.

The specimen can be analyzed both wet and dry. The dry specimen requires no further preparation. The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved. The wet specimen is dosed with total of 7 ml of the test solution as detailed below The liquid dose is added using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 50 Hz during all compression/decompression cycles.

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps 3001. Referring to FIG. 9A, place the dry specimen with its longitudinal edges (i.e., the 100 mm long edges) within the clamps. With the dry specimen laterally centered, securely fasten both edges in the clamps. Referring to FIG. 9B, move the right platform 3002b toward the stationary platform 3002a a distance of 20 mm so that a separation of 30.0 mm between the left and right clamps is achieved. Allow the dry specimen to bow upward as the movable platform is positioned. Now manually lower the probe 2001 until the bottom surface is approximately 1 cm above the top of the bowed specimen.

Figure 10A:
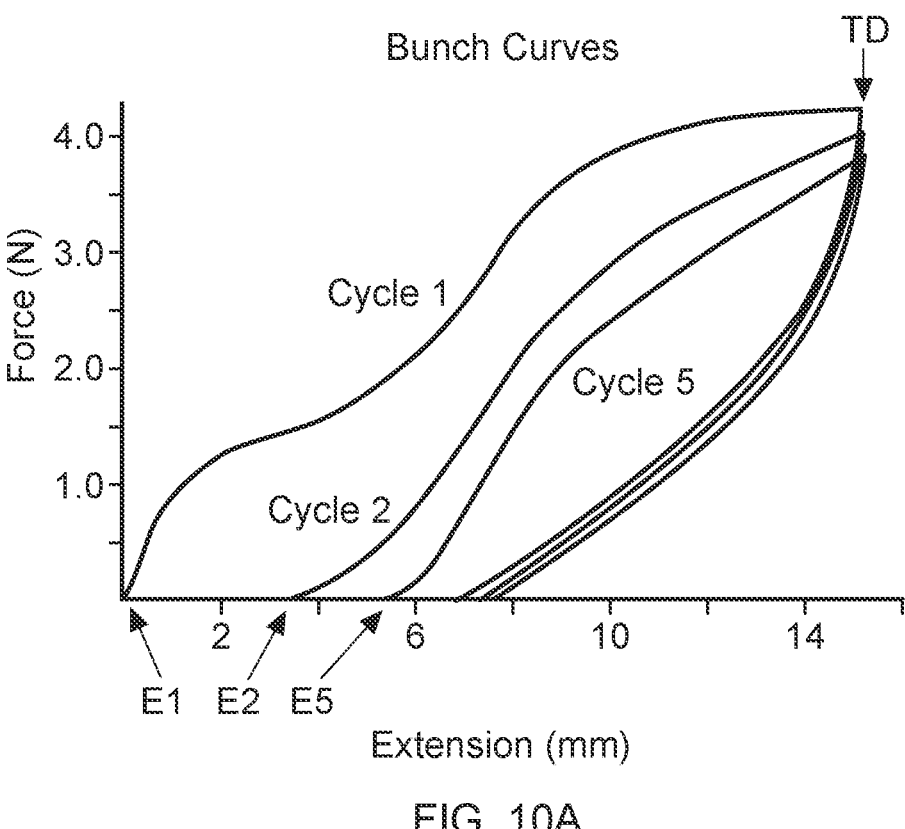
FIGS. 10A and 10B are illustrative graphs of Bunch Curves resulting from the Wet and Dry Bunched Compression Test. The graphs in FIGS. 10A and 10B are shown to illustrate how the calculations in the method may be performed and do not represent the data described herein.
Figure 10B:
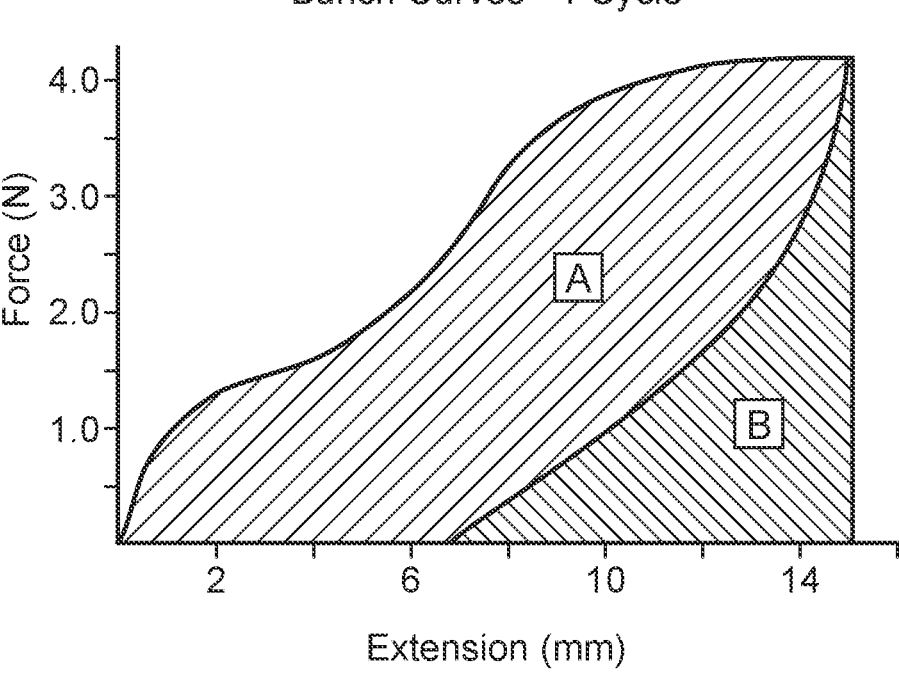

Start the test and continuously collect force (N) versus displacement (mm) data for all five cycles. Construct a graph of force (N) versus displacement (mm) separately for all cycles. A representative curve is shown in FIG. 10A. From the curve, determine the Dry Maximum Compression Force for each Cycle to the nearest 0.01 N, then multiply by 101.97 and record to the nearest 1 gram-force. Calculate the Dry % Recovery between the First and Second cycle as (TD–E2)/(TD–E1)*100 where TD is the total displacement and E2 is the extension on the second compression curve that exceeds 0.02 N, and record to the nearest 0.01%. In like fashion calculate the Dry % Recovery between the First Cycle and other cycles as (TD–E1)/(TD–E1)*100 and record to the nearest 0.01%. Referring to FIG. 10B, calculate the Dry Energy of Compression for Cycle 1 as the area under the compression curve (i.e., area A+B) and record to the nearest 0.1 N-mm Calculate the Dry Energy Loss from Cycle 1 as the area between the compression and decompression curves (i.e., Area A) and record to the nearest 0.1 N-mm Calculate the Dry Energy of Recovery for Cycle 1 as the area under the decompression curve (i.e., Area B) and report to the nearest 0.1 N-mm. In like fashion calculate the Dry Energy of Compression (N-mm), Dry Energy Loss (N-mm) and Dry Energy of Recovery (N-mm) for each of the other cycles and record to the nearest 0.1 N-mm. In like fashion, analyze a total of five replicate dry test specimens and report the arithmetic mean among the five dry replicates for each parameter as previously described, including basis weight.

The overall procedure is now repeated for a total of five replicate wet test specimens, reporting results for each of the five cycles as the arithmetic mean among the five wet replicates for Wet Maximum Compression Force to the nearest 1 gram-force for each cycle, Wet Energy of Compression to the nearest 0.1 N-mm for each cycle, Wet Energy Loss to the nearest 0.1 N-mm for each cycle, Wet Energy of Recovery to the nearest 0.1 N-mm for each cycle and Wet % recovery for each cycle. Of particular importance is the 5$^{th}$ cycle wet energy of recovery and 5$^{th}$ cycle wet % recovery properties from this test method.

CD Cyclic Elongation to 3% Strain

The cyclic tensile and recovery response of absorbent article specimens are measured for ten cycles of load application ("elongation") and load removal ("recovery") using a universal constant rate of extension test frame. The test specimen is cycled ten times to 3% engineering strain, then back to zero engineering strain. For each cycle, stiffness, peak load, normalized energy to peak, normalized recovery energy, strain at start of cycle, and strain at end of cycle (i.e., "permanent strain") are calculated and reported. The intention of this method is to understand the ability of samples to stretch in the x-y plane as a result of bodily forces, and then recover to their original state. All measurements are performed in a laboratory maintained at 23° C.±2 C.° and 50%±2% relative humidity and test specimens are conditioned in this environment for at least 2 hours prior to testing.

A suitable universal constant rate of extension test frame is the MTS Alliance interfaced to a computer running TestSuite control software (available from MTS Systems Corp, Eden Prairie, MN), or equivalent. The universal test frame is equipped with a load cell for which forces measured are within 1% to 99% of the limit of the cell. The fixtures used to grip the test specimen are lightweight (<80 grams), vise action clamps with knife or serrated edge grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any residual of folds or wrinkles. The test specimen is as long as the lateral length of the article (parallel to the lateral axis of the article, or the intended lateral axis of the article). When excising specimens from absorbent articles of different sizes and widths, the total specimen length (L$_{total}$) may vary from product to product, thus the results will be normalized to compensate for this variation. The test specimen has a width of 25.4 mm wide (parallel to the longitudinal axis, or intended longitudinal axis of the article). Specimen width (w)=25.4 mm Measure and record the total specimen length (L$_{total}$) to the nearest 0.1 mm. In like fashion, five replicate test specimens are prepared.

Measure the thickness (t) of the test specimen using a manually-operated micrometer equipped with a pressure foot capable of exerting a steady pressure of 0.1 psi±0.01 psi. The manually-operated micrometer is a dead-weight type instrument with readings accurate to 0.01 mm A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as specimen thickness (t) to the nearest 0.01 mm.

Prepare the universal test frame as follows. Set the initial grip to grip separation distance to a nominal gage length ($L_{nominal}$) that is shorter than the total specimen length and such that the specimen can be gripped securely at both ends (i.e., $L_{nominal} < L_{total}$) Then zero the crosshead. Program the test frame to move the grips closer together by an intentional slack of 1 mm to ensure no pretension force exists on the test specimen at the onset of the test. (During this motion, the specimen will become slack between the tensile grips.) Next, the grips will move apart at a slack speed of 1 mm/s until the slack preload of 0.05 N is exceeded. At this point, the following are true. 1) The crosshead position signal (mm) is defined as the specimen slack ($L_{slack}$) 2) The initial specimen gage length ($L_0$) is calculated as the nominal gage length plus the slack $L_0 = L_{nominal} + L_{slack}$, where units are in millimeters. 3) The crosshead extension ($\Delta L$) is set to zero (0.0 mm). 4) The crosshead displacement (mm) is set to zero (0.0 mm). At this position the engineering strain is zero, 0.0. Engineering strain is calculated as the change in length ($\Delta L$) divided by the initial length ($L_0$). Engineering strain=$\Delta L/L_0$. For one test cycle, the grips move apart at the initial speed of 1 mm/s until the engineering strain endpoint of 0.03 mm/mm is exceeded, immediately followed by the grips moving toward each other at the initial speed of 1 mm/s until the crosshead signal becomes less than the crosshead return position of 0 mm. The test cycle is repeated until a total of 10 cycles is complete.

The test is executed by inserting the test specimen into the grips such that the long axis of the specimen is parallel and centered with the motion of the crosshead. Start the test and continuously collect time, force and displacement data at a data acquisition rate of 100 Hz.

Construct a graph of load (N) versus displacement for all ten cycles. For each cycle, perform the following. Record peak load to the nearest 0.01 N. Calculate the energy to peak ($E_{peak}$) as the area under the load versus displacement curve from the cycle start to the strain endpoint of 0.03 mm/mm (during the loading portion of the cycle) and record to the nearest 0.01 N*mm Calculate the return energy ($E_{return}$) as the area under the load versus displacement curve from the strain endpoint of 0.03 mm/mm to the crosshead return of 0 mm (during the unloading portion of the cycle) and record as recovery energy to the nearest 0.01 N*mm Calculate the normalized energy to peak ($NE_{peak}$) as the energy to peak divided by the initial length, where $NE_{peak} = E_{peak}/L_0$, and record to the nearest 0.01 mN. Calculate the normalized return energy ($NE_{return}$) as the return energy divided by the initial length ($NE_{return} = E_{return}/L_0$), and record to the nearest 0.01 mN. Units of $NE_{peak}$ and $NE_{return}$ are milliNewtons (mN).

Now construct a graph of engineering stress ($\sigma$) versus engineering strain for all ten cycles, and for each cycle perform the following. Engineering stress, in units of $N/mm^2$, is the load divided by the cross sectional area of the specimen, where the cross sectional area is the specimen width (w) multiplied by the thickness (t), $\sigma = Load/(w*t)$. Determine the modulus, or slope of the stress versus strain curve for a line between the point that occurs at the minimum force and the point that occurs at the maximum force (during the loading portion of the cycle) and record as modulus to the nearest 0.01 N/mm Calculate stiffness by multiplying the modulus by the specimen thickness and record as tensile stiffness to the nearest 0.01 N/mm. The strain of the test specimen at the beginning of the cycle is defined by the strain when the slack preload of 0.05 N is exceeded for that cycle (during the loading portion of the cycle), and is recorded as cycle initial strain to the nearest 0.01 mm/mm. The strain of the test specimen at the end of the cycle is defined by the strain when the load becomes less than the preload of 0.05 N for that cycle (during the unloading portion of the cycle), and is recorded as permanent strain to the nearest 0.01 mm/mm. In like fashion, the overall procedure is now repeated for all five replicates.

The arithmetic mean among the five replicate test specimens is calculated for each of the parameters, for each of the ten cycles, and reported as Peak Load to the nearest 0.01 N, Normalized Energy to Peak to the nearest 0.01 mN, Normalized Recovery Energy to the nearest 0.01 mN, Tensile Stiffness to the nearest 0.01 N/mm, Cycle Initial Strain to the nearest 0.01 mm/mm, and Permanent Strain to the nearest 0.01 mm/mm Structural Bond Sites Pattern Spacing and Area Measurement Method The spacing between the discreet structural bond sites that are used to create a quilt-like pattern on absorbent article samples, and the overall area taken up by the sum of those elements in a specified region of the sample are measured on images of the absorbent article sample acquired using a flatbed scanner. The scanner is capable of scanning in reflectance mode at a resolution of 2400 dpi and 8 bit grayscale. A suitable scanner is an Epson Perfection V750 Pro from Epson America Inc., Long Beach CA, or equivalent. The scanner is interfaced with a computer running an image analysis program. A suitable program is ImageJ v. 1.52, National Institute of Health, USA, or equivalent. The sample images are distance calibrated against an acquired image of a ruler certified by NIST. To enable maximum contrast, the specimen is backed with an opaque, black background of uniform color prior to acquiring the image. All testing is performed in a conditioned room maintained at about 23±2° C. and about 50±2% relative humidity.

The test sample is prepared as follows. Remove the absorbent article from any wrapper present. If the article is folded, gently unfold it and smooth out any wrinkles. If wings are present, extend them but leave the release paper intact. The test samples are conditioned at about 23° C.±2 C.° and about 50%±2% relative humidity for 2 hours prior to testing.

Images are obtained as follows. The ruler is placed on the scanner bed such that it is oriented parallel to the sides of the scanner glass. An image of the ruler (the calibration image) is acquired in reflectance mode at a resolution of 2400 dpi (approximately 94 pixels per mm) and in 8-bit grayscale. The calibration image is saved as an uncompressed TIFF format file. After obtaining the calibration image, the ruler is removed from the scanner glass and the test sample is scanned under the same scanning conditions as follows. Place the test sample onto the center of the scanner glass and secure, if necessary, such that it lies flat with the body-facing surface of the sample facing the scanner's glass surface. The sample is oriented in such a way that the entire sample is within the glass surface. The black background is placed on top of the specimen, the scanner lid is closed, and a scanned image of the entire sample is acquired with the same settings as used for the calibration image. The sample image is saved as an uncompressed TIFF format file.

The sample image is analyzed as follows. Open the calibration image file in the image analysis program, and calibrate the image resolution using the imaged ruler to determine the number of pixels per millimeter. Now open the sample image in the image analysis program, and set the distance scale using the image resolution determined from the calibration image. Now visually inspect the pattern of emboss elements present on the sample in the image and identify the zones of the pattern that are to be analyzed. For example the absorbent article can be divided into three equal lengths zones in the machine direction such as the front one third zone, zone 1, the central one third zone, zone 2 and the end one third zone, zone 3 as example. Use the image analysis tools to draw a shape along the outer perimeter of the first discreet zone to be analyzed. Measure the area of this first zone and record as Zone 1 Total Area to the nearest 0.01 mm². Now measure the area of each individual, discreet emboss element that lies inside of the zone 1 perimeter as follows. Draw a minimum bounding circle around an individual emboss element such that no portion of the emboss element lies outside of the bounding circle. Now measure the area of the bounding circle for that emboss element and record the emboss element area to the nearest 0.01 mm². In like fashion, measure the area of every emboss element, including portions of emboss elements, that lie inside zone 1 and record each to the nearest 0.01 mm². Now sum the areas of all of the emboss elements inside of zone 1 and record as Zone 1 Total Emboss Element Area to the nearest 0.01 mm². Divide the Zone 1 Total Emboss Element Area by the Zone 1 Total Area then multiply by 100 and record as Zone 1% Total Area Represented by Emboss Elements. The spacing between each discreet emboss element inside of zone 1 is measured as follows. Measure the distance from the center of the minimum bounding circle drawn around a discreet emboss element inside of zone 1, as described herein, to the center of the minimum bounding circle drawn around the nearest neighboring discreet emboss element inside of zone 1, and record this distance as emboss spacing to the nearest 0.01 mm. In like fashion, repeat for all neighboring emboss elements inside of zone 1, and record each distance to the nearest 0.01 mm Now calculate the arithmetic mean among all measured emboss spacings measured between nearest neighbors inside of zone 1, and record as Zone 1 Emboss Spacing to the nearest 0.01 mm.

In like fashion, the entire procedure is repeated for each additional zone containing emboss elements that is present on the test sample and label accordingly as Zone 2, Zone 3, etc.

Light Touch Rewet Method

Light Touch Rewet method is a quantitative measure of the mass of liquid that emerges from an absorbent article test sample that has been dosed with a specified volume of Artificial Menstrual Fluid (AMF; as described herein) when a weight is applied for a specified length of time. All measurements are performed in a laboratory maintained at 23° C.±2 C.° and 50%±2% relative humidity.

A syringe pump equipped with a disposable syringe is utilized to dose the test sample. A suitable pump is the Perfusor® Compact S (available from B. Braun), or equivalent, and must be able to accurately dispense the AMF at a rate of 42 ml/min. The disposable syringe is of ample volume (e.g., BD Plastipak 20 mL) and is connected to flexible tubing that has an inner diameter of 3/16" (e.g., Original Perfusor® Line, available from Braun, or equivalent). The AMF is prepared, as described herein, and is brought to room temperature (23° C.±2 C.°) prior to using for this test. Prior to the commencement of the measurement, the syringe is filled with AMF and the flexible tubing is primed with the liquid, and the dispensing rate (42 ml/min) and dosing volume (4.0 mL+0.05 mL) are verified according to the manufacturer's instructions. The flexible tubing is then mounted such that it is oriented vertically above the test sample, and the distance between the tip of the tubing and the surface of the test sample is 19 mm. To note, the AMF must be removed from the syringe and thoroughly mixed every 15 minutes.

The rewet weight assembly consists of an acrylic plate and a stainless steel weight. The acrylic plate has dimensions of 65 mm by 80 mm with a thickness of about 5 mm. The stainless steel weight along with the acrylic plate have a combined mass of 2 pounds (907.19 g), to impart a pressure of 0.25 psi beneath the surface of the acrylic plate.

For each test sample, five sheets of filter paper with dimensions of 4 inch by 4 inch are used as the rewet substrate. The filter paper is conditioned at 23° C.±2 C.° and 50%±2% relative humidity for at least 2 hours prior to testing. A suitable filter paper has a basis weight of about 139 gsm, a thickness of about 700 microns with an absorption rate of about 1.7 seconds, and is available from Ahlstrom-Munksjo North America LLC, Alpharetta, GA VWR International as Ahlstrom grade 989, or equivalent.

Prepare the test sample as follows. The test samples are conditioned at 23° C.±2 C.° and 50%±2% relative humidity for at least 2 hours prior to testing. Test samples are removed from all packaging using care not to press down or pull on the products while handling. Lay the test sample on a horizontally rigid flat surface and gently smooth out any folds. Determine the test location as follows. For symmetrical samples (i.e., the front of the sample is the same shape and size as the back of the sample when divided laterally along the midpoint of the longitudinal axis of the sample), the test location is the intersection of the midpoints of the longitudinal axis and lateral axis of the sample. For asymmetrical samples (i.e., the front of the sample is not the same shape and size as the back of the sample when divided laterally along the midpoint of the longitudinal axis of the sample), the test location is the intersection of the midpoint of the longitudinal axis of the sample and a lateral axis positioned at the midpoint of the sample's wings. A total of three test samples are prepared.

Place the test sample on a horizontally flat rigid surface, with the previously identified test location centered directly below the tip of the flexible tubing. Adjust the height of the tubing such that it is 19.0 mm above the surface of the test sample. Start the pump to dispense 4.0 mL+0.05 mL of AMF at a rate of 42 ml/min. As soon as the AMF has been fully dispensed, start a 10 minute timer. Now obtain the mass of 5 sheets of the filter paper and record as dry mass to the nearest grams. When 10 minutes have elapsed, place the five sheets of pre-weighed filter papers onto the test sample, centering the stack over the dosing location. Now place the acrylic plate centered over the top of the filter papers such that the long side of the plate is parallel with the longitudinal axis of the test sample. Now carefully lower the stainless steel weight centered over the acrylic plate and immediately start a 30 second timer. After 30 seconds have elapsed, gently remove the rewet weight and acrylic plate and set aside. Obtain the mass of the five sheets of filter paper and record as wet mass to the nearest 0.001 grams. Subtract the dry mass from the wet mass of the filter papers, and record as rewet to the nearest 0.001 grams. Wipe off any residual test liquid from the bottom face of the acrylic plate prior to testing the next sample. In like fashion, repeat for a total of three replicate test samples.

The arithmetic mean of the rewet among the three replicate test samples is calculated and reported as the 'Light Touch Rewet' to the nearest 0.001 g.

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity of the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, sterilized, available from American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Examples/Data

The following data and examples, including comparative examples, are provided to help illustrate the upper and lower nonwoven layers, absorbent core structures and/or absorbent articles described herein. The exemplified structures are given solely for the purpose of illustration and are not to be construed as limitations of the present disclosure, as many variations thereof are possible without departing from the spirit and scope of the invention.

Nonwoven Material Test

Nonwoven layer materials are tested to assess the ability of the nonwoven material to strain (elongate) with a balanced stretch and to recover to their original state (simulating in-use physical deformation). Samples F-H are comparative examples. The test is performed according to the CD Cyclic Elongation to 3% Strain Method and the Strain to Break Method described herein. The results are shown in Table 1.

TABLE 1

| | Nonwoven Materials tested in the CD Cyclic Elongation to 3% Strain Method and the Strain to Break Method | | | | |
|---|---|---|---|---|---|
| Sample | Nonwoven Material | Fiber Composition | Tensile Stiffness N/mm | Permanent Strain mm/mm | % Strain to Break % |
| A | 40 gsm Carded Resilient Nonwoven[1] | BiCo (PE/PET) - 60% 2 DTex/ 40% 4 DTex Blend | 0.30 | 0.0060 | >10% |

TABLE 1-continued

Nonwoven Materials tested in the CD Cyclic Elongation
to 3% Strain Method and the Strain to Break Method

| Sample | Nonwoven Material | Fiber Composition | Tensile Stiffness N/mm | Permanent Strain mm/mm | % Strain to Break % |
|---|---|---|---|---|---|
| B | 55 gsm Resilient Spunlace 1[2] | 30% 10 DTex HS-PET; 20% 1.3 DTex Rayon; 50% 2.2 DTex BiCo (PE/PET) | 1.57 | 0.0064 | >10% |
| C | 50 gsm Resilient Spunlace 6[3] | 20% 1.3 DTex Rayon; 20% 3.3 DTex tri-lobal Rayon; 60% 5.8 DTex PE/PET | 1.50 | 0.0054 | >10% |
| D | 24 gsm Carded Nonwoven[4] | 100% 2 DTex BiCo (PE/PET) | 0.16 | 0.0160 | >10% |
| E | 55 gsm Resilient Spunlace 5[5] | 40% 1.7 DTex/38 mm Rayon; 40% 2.2 DTex PET; 20% 10 DTex HS PET | 0.31 | 0.0127 | >10% |
| F | 18 gsm Spunbond Nonwoven[6] | 100% 2.0 DTex PP | 0.24 | 0.0096 | >10% |
| G | 25 gsm Spunbond Nonwoven[7] | 100% 2.0 Dtex PP | 0.37 | 0.0093 | >10% |
| H | 17 gsm Tissue[8] | 100% Cellulose | 1.72 | 0.0137 | <5% |

[1]Available as ATB Z87G-40 from Xiamen Yanjan New Material Co. (China)
[2]Available as Sawasoft ® 53FC041001 from Sandler GmbH (Germany)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[7]Available as PEGZN25 BICO7030 Phobic from dPFNonwovens Czech S.R.O (Czech Republic)
[8]Available as 3028 from DunnPaper (USA)

It is found that suitable nonwoven layer materials strain (elongate) with a balanced stretch vs. recovery behavior. If the nonwoven layer material elongates plastically (i.e., stretches but does not recover) as the fluff/AGM matrix in the inner core layer elongates, there will be insufficient recovery energy to return to the initial, pre-stretched state and the nonwoven layer material will become permanently strained (stretched). The upper nonwoven layers of the present disclosure can have a Permanent Strain value of less than about 0.013. At the same time, if the nonwoven layer material is strained aggressively, for example greater than 5%, the nonwoven layer material needs to retain its integrity and not tear or break (see, for example, Sample H which tears and has a Strain to Break of less than 5%). Nonwoven layers of the present disclosure can have a Strain to Break of greater than about 10%.

The nonwoven layer materials described above are also tested to assess the ability of nonwoven materials to bend and deform and to recover to their original state. The test is performed according to the Wet and Dry CD Ultra Sensitive 3 Point Bending Method described herein. The results are shown in Table 2.

TABLE 2

Nonwoven Materials Tested in the Wet and Dry
CD Ultra Sensitive 3 Point Bending Method

| Sample | Dry Peak Load N | Dry Bending Energy N*mm | Dry Recovery Energy N*mm |
|---|---|---|---|
| A | 0.07 | 0.219 | 0.092 |
| B | 0.38 | 1.015 | 0.291 |
| C | 0.26 | 0.595 | 0.201 |
| D | 0.09 | 0.176 | 0.036 |

TABLE 2-continued

Nonwoven Materials Tested in the Wet and Dry
CD Ultra Sensitive 3 Point Bending Method

| Sample | Dry Peak Load N | Dry Bending Energy N*mm | Dry Recovery Energy N*mm |
|---|---|---|---|
| E | 0.03 | 0.059 | 0.032 |
| F | 0.01 | 0.0216 | 0.005 |
| G | 0.03 | 0.0624 | 0.019 |
| H | 0.04 | 0.0734 | 0.031 |

During walking, an absorbent article is compressed and bent side-to-side in a cyclic pattern as the gap between her legs narrows and then expands with her leg motions. Without being limited by theory, it is believed that a nonwoven layer material having a Dry Bending Energy of less than about 2 N*mm will allow this bending compression to occur readily yet will not be so stiff as to hinder the bending compression. At the same time, following the bending compression, the nonwoven layer needs to be able to sustain sufficient dry recovery energy to return the nonwoven layer and the fluff/AGM matrix in the inner core layer back to its initial, pre-bent state. The upper nonwoven layers of the present disclosure can have a Dry Recovery Energy value of greater than about 0.03 N*mm.

Samples A-E exhibit a Dry Peak Load of from 0.03N to 0.38N and a Dry Recovery Energy of from 0.032 to 0.092 N*mm, demonstrating that these materials readily bend and have sufficient dry recovery energy to recover their initial, pre-bent state. Samples F and G, which are comparative examples, exhibit a Dry Peak Load of 0.01N and 0.03N, respectively, and a Dry Recovery Energy of 0.005 N*mm and 0.019 N*mm, respectively, demonstrating that while these materials readily bend, they do not have sufficient recovery energy to recover their initial, pre-bent state after compression. Sample H (comparative example) exhibits a Dry Peak Load of 0.04 N and a Dry Recovery Energy of 0.031 N*mm. However, it is found that Sample H tears when it becomes wet, making it insufficient to function as an upper and/or lower nonwoven layer of the present disclosure.

Without being limited by theory, it is believed that non-woven layer materials comprising thick fibers (from about 2.0 Dtex to about 10 Dtex) that are arranged within a network structure are able to carry the mechanical load within the fiber network and return the absorbent core structure and/or absorbent article to its initial shape follow-ing bending compression. Samples F and G comprise rela-tively fine fibers (less than about 2.0 Dtex), while Samples A-E comprise fiber blends having a fiber thickness of from about 2.2 Dtex to about 10 Dtex.

Absorbent Core Structure Test

Absorbent cores structures are tested to assess the ability of the absorbent core structure to compress (simulating the compressions experienced between a wearer's legs) and to recover to their original state. Examples 1-3 in Table 3 illustrate absorbent core structures described herein. Comp. Ex. A-C are comparative examples. A description of Ex. 1-3 and Comp. Ex. A-C are listed in Table 3. The absorbent core structures are prepared as described hereafter. The absorbent core structures are evaluated according to the Wet and Dry Bunched Compression Method as described herein. The results are shown in Table 4.

TABLE 3

Absorbent Core Structures

| Example | Upper Nonwoven Layer | Inner Core Layer | Lower Nonwoven Layer |
|---|---|---|---|
| Ex. 1 | 40 gsm Carded Resilient Nonwoven[1] | 175 gsm Fluff[10]/ 70 gsm AGM[9] | 18 gsm Spunbond Nonwoven[6] |
| Ex. 2 | 55 gsm Resilient Spunlace 5[5] | 175 gsm Fluff[10]/ 70 gsm AGM[9] | 18 gsm Spunbond Nonwoven[6] |
| Ex. 3 | 50 gsm Resilient Spunlace 6[3] | 175 gsm Fluff[10]/ 70 gsm AGM[9] | 40 gsm Carded Nonwoven[1] |
| Comp. Ex. A | 24 gsm Carded Nonwoven[4] | 175 gsm Fluff[10]/ 70 gsm AGM[9] | 10 gsm SMS Nonwoven[11] |
| Comp. Ex. B | 17 gsm Tissue[8] | 175 gsm Fluff[10]/ 70 gsm AGM[9] | 17 gsm Tissue[8] |
| Comp. Ex. C | 17 gsm Tissue[8] (10 × 10 bonding) | 175 gsm Fluff[10]/ 70 gsm AGM[9] | 17 gsm Tissue[8] |

[1]Available as ATB Z87G-40 from Xiamen Yanjan New Material Co. (China)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[8]Available as 3028 from DunnPaper (USA)
[9]Available as Favor SXM9745 from Evonik (Germany)
[10]Available as Item 9E3-COOSABSORB S from Resolute Alabama (USA)
[11]Available as Article 4004416 (MR 3585374) from Fitesa (Germany)

The absorbent core structures listed in Table 3 are pro-duced as detailed within the specification. Specifically, the upper nonwoven layer is first introduced onto the forming drum within the laydown section, and under vacuum it is drawn into the 3 dimensional pocket shape. A homogeneous stream of the fluff (cellulose) and AGM material is deposited onto the upper nonwoven layer directly within the forming station. Prior to entering the forming station, the upper nonwoven is coated with a spray adhesive (Technomelt DM 9036U available from Henkel, (Germany), 6 gsm continuous meltblown spirals, 50 mm wide) to provide a stronger connection of the fluff (cellulose) and AGM to the upper nonwoven layer without hindering the flow of liquid into the fluff/AGM matrix. On exiting the laydown section, the lower nonwoven web is combined with the nonwoven carrying the homogeneous blend of fluff/AGM. This lower nonwoven is precoated with adhesive (Technomelt DM 9036U available from Henkel (Germany)) to enable a perimeter seal (10 gsm meltblown spirals, 20 mm wide on the sides) and in the center a 6 gsm, 50 mm wide continuous meltblown spiral adhesive (Technomelt DM 9036U available from Henkel (Germany)) is applied to better integrate the fluff/AGM matrix.

Figure 4:
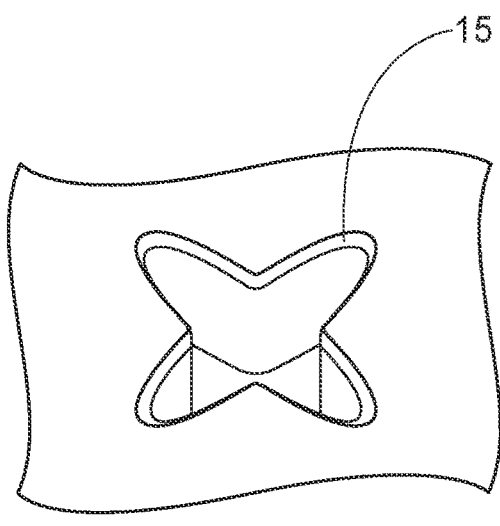
FIG. 4 is a close up illustration of a structural bond site in accordance with the present disclosure.

Ex. 1 through 3 and Comp. Ex. A and B also have the structural bonds shown in FIG. 4 with the profile shown in FIG. 5. Ex. 1-3 and Comp. Ex. A-B have a structural bond spacing of 32 mm×16 mm, thereby occupying a total struc-tural bond site area of 1.38% of the total area of the absorbent core structure. Comp Ex. C is identical to Comp. Ex. B except the structural bond spacing is 10 mm×10 mm, thereby occupying a total structural bond site area of 6.28% of the total area of the absorbent core structure. The struc-tural bonds are applied with a heated aluminum die to create an emboss pattern within a heated hydraulic press. The structural bond embosser plate has protrusions of an area of 3.55 mm² and about 1 mm in height as shown in FIG. 4 with the profile shown in FIG. 5. The structural bonds are spaced according to the dimensions of separation described above. The structural bond embosser plate is heated to 120° C. and set to a compression pressure of 170 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Ex. 1-3 and Comp. Ex. A-C also have flex bond channel regions applied with the pattern shown in FIG. 2C. The flex bond channel regions are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated under-neath the heated embosser plate on the hydraulic press bottom plate and a sheet of thin Teflon™ film is placed over the sample prior to embossing to avoid melting of the topsheet fibers. The hydraulic press is activated and com-presses the sample for a dwell time of 1.7 seconds to create the emboss pattern.

TABLE 4

Absorbent Core Structures Measured in the
Wet and Dry Bunched Compression Method

| | Wet and Dry Bunched Compression Method | |
|---|---|---|
| Example | 5th Cycle Wet Maximum Compression Force (gf) | 5th Cycle Wet Energy of Recovery (N*mm) |
| Ex. 1 | 208 | 1.30 |
| Ex. 2 | 207 | 1.07 |
| Ex. 3 | 213 | 1.76 |
| Comp. Ex. A | 136 | 0.26 |
| Comp. Ex. B | 129 | 0.59 |
| Comp. Ex. C | 86 | 0.32 |

It is found that absorbent core structures comprising nonwoven layer materials that have sufficient resiliency and recovery energy are able to recover to the original, pre-compression absorbent core structure shape. Ex. 1-3 exhibit a $5^{th}$ Cycle Wet Energy of Recovery of greater than 1.0 N*mm and a $5^{th}$ Cycle Wet Maximum Compression Force of from 207 gf to 213 gf. These structures exhibit a low force to compress (less resistance so it feels soft and flexible), yet are still able to recover their shape as the structure is compressed and released in a cyclic fashion. However, Comp. Ex. A-C exhibit a $5^{th}$ Cycle Wet Energy of Recovery of from 0.26 to 0.59 N*mm Without sufficient recovery energy after five cycles of compression, Comp. Ex. A-C remain in a compressed, bunched state with insufficient force (stored energy) to recover its original, pre-compression shape.

Absorbent core structures and/or absorbent articles of the present disclosure can have a $5^{th}$ Cycle Wet Energy of the compressions experienced between a wearer's legs) and to recover to their original state. Ex. 4-7 illustrate absorbent articles described herein. Comp. Ex. D and E are comparative examples. Comp. Ex. F-L are in-market finished products. A description of Ex. 4-7 and Comp. Ex. D-E are listed in Table 5a. A description of Comp. Ex. F-L is listed in Tables 5b and 5c. Ex. 4-7 and Comp. Ex. D and E are prepared as described hereafter. The absorbent articles in Table 5a and 5b are evaluated according to the Wet and Dry CD and MD 3 Point Bend Method, the Wet and Dry Bunched Compression Method, and the Light Touch Rewet Method as described herein. The results are shown in in Table 6.

TABLE 5a

| | | Absorbent Article Description | | |
| | | Absorbent core structure | | |
| Example | Topsheet | Upper Nonwoven Layer | Inner Core Layer | Lower Nonwoven Layer |
|---|---|---|---|---|
| Ex. 4 | Nonwoven SG[12] | 40 gsm Carded Resilient Nonwoven[1] | 175 gsm Fluff[10]/ 70 gsm AGM9 | 18 gsm Spunbond Nonwoven[6] |
| Ex. 5 | Nonwoven SG[12] | 55 gsm Resilient Spunlace 5[5] | 175 gsm Fluff[10]/ 70 gsm AGM9 | 18 gsm Spunbond Nonwoven[6] |
| Ex. 6 | Nonwoven SG[12] | 50 gsm Resilient Spunlace 6[3] | 175 gsm Fluff[10]/ 70 gsm AGM9 | 18 gsm Spunbond Nonwoven[6] |
| Ex. 7 | Nonwoven SG[12] | 55 gsm Resilient Spunlace 1[2] | 175 gsm Fluff[10]/ 70 gsm AGM9 | 18 gsm Spunbond Nonwoven[6] |
| Comp. Ex. D | Nonwoven SG[12] | 24 gsm Carded Nonwoven[4] | 175 gsm Fluff[10]/ 70 gsm AGM9 | 18 gsm Spunbond Nonwoven[6] |
| Comp. Ex. E | Nonwoven SG[12] | 17 gsm Tissue[8] | 175 gsm Fluff[10]/ 70 gsm AGM9 | 17 gsm Tissue[8] |

[1] Available as ATB Z87G-40 from Xiamen Yanjan New Material Co. (China)
[2] Available as Sawasoft ® 53FC041001 from Sandler GmbH (Germany)
[3] Available as Sawasoft ® 553FC041005 (option 82) from Sandler GmbH (Germany)
[4] Available as Aura 20 from Xiamen Yanjan New Material Co. (China)
[5] Available as S25000541R01 from Jacob Holms Industries (Germany)
[6] Available as PFNZN 18G BICO8020 PHI 6 from dPFNonwovens Czech S.R.O (Czech Republic)
[8] Available as 3028 from DunnPaper (USA)
[9] Available as Favor SXM9745 from Evonik (Germany)
[10] Available as Item 9E3-COOSABSORB S from Resolute Alabama (USA)
[12] The nonwoven topsheet "Nonwoven SG" is a nonwoven web according to U.S. Patent Publication No. 2019/0380887.

Recovery of greater than about 1.0 N*mm, or from about 1.0 to about 3.5 N*mm Absorbent core structures and/or absorbent articles of the present disclosure can have a $5^{th}$ Cycle Wet Maximum Compression Force of greater than about 150 gf, preferably greater than about 200 gf, or from about 150 gf to about 225 gf.

It is found that while an individual nonwoven material may have sufficient % Strain to Break in the Strain to Break Method, once combined into an absorbent core structure, the nonwoven material may not be capable of providing sufficient recovery energy for the full absorbent core structure (such as, for example in Comp. Ex. A) to return to its original, pre-compression shape. For instance, in Comp. Ex. A, the basis weight and thickness of the fibers of the upper nonwoven material when combined with the thin lower nonwoven material provides a $5^{th}$ Cycle Wet Energy of Recovery of less than 1.0 N*mm.
Finished Product Test Absorbent articles are tested to assess the ability of a wrapped absorbent core structure to compress (simulating TABLE 5b

| | In-Market Finished Products: | | |
| Example | In-Market Product | Size | Where Produced |
|---|---|---|---|
| Comp. Ex. F | Always Ultra | Size 2 | Canada |
| Comp. Ex. G | Stayfree Ultra | Size Long | USA |
| Comp. Ex. H | U by K (Kotex Security) | Size Long | USA |
| Comp. Ex. I | Body Form | Size Long | UK |
| Comp. Ex. J | Kao Laurier F | Size Long | Japan |
| Comp. Ex. K | Unicharm Sofy Naked Feel | Size regular | Japan |
| Comp. Ex. L | Always Infinity | Size 2 | Canada |

TABLE 5c

Materials Found in the In-Market Products (Comp. Ex. F to L)

| In-Market Products | Topsheet | First Acquisition Layer | Fluid Storage Layer | Other |
|---|---|---|---|---|
| Comp. Ex. F | Formed Film | 55 gsm Spunlace | 163 gsm Airlaid | n/a |
| Comp. Ex. G | Spunbond Nonwoven | Airlaid Secondary Topsheet | Fluff/AGM core densified | n/a |
| Comp. Ex. H | Spunbond Nonwoven | Airlaid Secondary Topsheet | Tissue wrapped Fluff/AGM core - densified | Additional cellulose oval element under topsheet |
| Comp. Ex. I | Spunbond Nonwoven | Airlaid Secondary Topsheet | Fluff/AGM core - densified | n/a |
| Comp. Ex. J | Carded Nonwoven | Carded Nonwoven | Tissue wrapped fluff/AGM core | n/a |
| Comp. Ex. K | Carded Nonwoven | Carded Nonwoven | Tissue wrapped fluff/AGM core | n/a |
| Comp. Ex. L | Spunbond Nonwoven | High Internal Phase Foam | High Internal Phase Foam | n/a |

Ex. 4 through 7 and Comp. Ex. D and E include structures as detailed for the Ex. 1 through 3 in Table 3 with the same adhesive designs and same 32 mm×16 mm structural bond pattern (a total structural bond site area of 1.38% of the total area of the absorbent core structure) in the absorbent core structure. Additionally, the absorbent articles include a non-woven topsheet web as detailed in US Patent Publication No. 2019/0380887 bonded to the absorbent core structure with a spray adhesive application (Technomelt DM 9036U available from Henkel (Germany), 3 gsm continuous melt-blown spirals, 50 mm wide, 150 mm long). In addition, a 12 gsm polypropylene backsheet is bonded to the outward-facing surface of the lower nonwoven with a spray adhesive application (Technomelt DM 9036U available from Henkel (Germany), 3 gsm continuous meltblown spirals, 50 mm wide, 150 mm long).

Ex. 4-7 and Comp. Ex. D and E also have the structural bonds shown in FIG. 4 with the profile shown in FIG. 5. The structural bonds are applied with a heated aluminum die to create an emboss pattern within a heated hydraulic press. The structural bond embosser plate has protrusions of an area of 3.55 mm² and about 1 mm in height as shown in FIG. 4 with the profile shown in FIG. 5. The structural bonds are spaced according to the dimensions of separation described above. The structural bond embosser plate is heated to 120°

C. and set to a compression pressure of 170 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Prior to bonding the backsheet, flex bond channel regions are applied to Ex. 4-7 and Comp. Ex. D and E with the pattern shown in FIG. 2C. The flex bond channel regions are applied with a heated aluminum die to create an emboss pattern within a heated hydraulic press. The channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern.

TABLE 6

Absorbent Articles and In-Market Finished Products Tested in the Wet and Dry CD and MD 3 Point Bend Method, the Wet and Dry Bunched Compression Method, and the Light Touch Rewet Method

| | Wet & Dry CD & MD 3 Point Bend Method | | | Wet and Dry Bunched Compression Method | | Light Touch |
|---|---|---|---|---|---|---|
| Example | Dry Caliper (mm) | CD Dry Modulus (N/mm²) | CD Dry Bending Stiffness (N · mm²) | 5th Cycle Wet Energy of Recovery (N · mm) | 5th Cycle Wet % Recovery % | Rewet Method Light Touch Rewet (g) |
| Ex. 4 | 2.61 | 0.21 | 14.9 | 2.76 | 36 | 0.070 |
| Ex. 5 | 3.35 | 0.09 | 13.5 | 1.68 | 29 | 0.075 |
| Ex. 6 | 3.53 | 0.07 | 13.0 | 1.50 | 31 | 0.047 |
| Ex. 7 | 2.74 | 0.22 | 18.7 | 3.15 | 34 | 0.10 |
| Comp. Ex. D | 3.76 | 0.06 | 13.0 | 1.70 | 27 | 0.17 |
| Comp. Ex. E | 3.44 | 0.08 | 9.1 | 1.29 | 24 | 0.31 |
| Comp. Ex. F | 2.13 | 1.39 | 54.5 | 0.7 | 43 | n/a |
| Comp. Ex. G | 3.05 | 0.41 | 47.5 | 3.1 | 24 | n/a |
| Comp. Ex. H | 2.66 | 0.43 | 30.8 | 2.0 | 28 | n/a |
| Comp. Ex. I | 2.62 | 0.52 | 39.4 | 3.0 | 27 | n/a |
| Comp. Ex. J | 4.84 | 0.10 | 49.4 | 4.8 | 35 | n/a |

TABLE 6-continued

Absorbent Articles and In-Market Finished Products Tested in
the Wet and Dry CD and MD 3 Point Bend Method, the Wet and Dry
Bunched Compression Method, and the Light Touch Rewet Method

| | Wet & Dry CD & MD 3 Point Bend Method | | | Wet and Dry Bunched Compression Method | | Light Touch |
| | Dry Caliper (mm) | CD Dry Modulus (N/mm$^2$) | CD Dry Bending Stiffness (N · mm$^2$) | $5^{th}$ Cycle Wet Energy of Recovery (N · mm) | $5^{th}$ Cycle Wet % Recovery % | Rewet Method Light Touch Rewet (g) |
| Example | | | | | | |
|---|---|---|---|---|---|---|
| Comp. Ex. K | 3.11 | 0.25 | 30.6 | 1.3 | 26 | n/a |
| Comp. Ex. L | 2.80 | 0.30 | 29 | 2.5 | 73 | n/a |

It is believed that in order to provide high bodily conformability, the absorbent article of the present disclosure can exhibit a low CD Dry Bending Stiffness (i.e., high flexibility) of from about 10 to about 30 N·mm$^2$, or from about 10 to about 25 N·mm$^2$. Also, it is believed that in order to provide an absorbent article that can compress with bodily motion and recover to its original, pre-compressed state against the user's body, the absorbent article of the present disclosure can have a $5^{th}$ Cycle Wet Energy of Recovery of from about 1.0 to about 3.5 N·mm and/or a $5^{th}$ Cycle Wet % Recovery of from about 29% to about 40%. Absorbent articles of the present disclosure can also maintain good fluid handling that delivers a low light touch rewet of from about 0 to about 0.15 g.

Ex. 4-7 exhibit a CD Dry Bending Stiffness of from 13.0 to 18.7 N·mm$^2$ and a $5^{th}$ Cycle Wet % Recovery in the Wet and Dry Bunched Compression Method of from 29 to 36%, demonstrating that these structures will be able to sustain their shape in use. Comp. Ex. D and E exhibit a CD Dry Bending Stiffness of 9.1 and 13.0 N·mm$^2$, respectively. However, Comp. Ex. D and E exhibit a $5^{th}$ Cycle Wet % Recovery in the Wet and Dry Bunched Compression Method that is less than 29%, demonstrating that these structures will be unable to sustain their shape in use and will remain shape. At the same time, the absorbent article (via the absorbent core structure) needs to recover along the same path as the compression to return to its pre-compression location. If the $5^{th}$ Cycle Wet Energy of Recovery is less than about 1.0 N·mm the absorbent article may not have the recovery energy needed to recover its shape. If the $5^{th}$ Cycle Wet Energy of Recovery value is too high, the recovery may be too forceful, leaving the wearer to feel like the absorbent article is not staying in place. If the $5^{th}$ Cycle Wet % Recovery value is low (less than about 29%), the absorbent article may not return to its pre-compression shape and may remain deformed and bunched. If the $5^{th}$ Cycle Wet % Recovery value is excessively high (greater than about 40%), it suggests that the absorbent article may recover too strongly to the flat shape when it is first applied to the wearer's panty as opposed to the shape against her body.

Structural Bond Test

Absorbent cores structures are tested to assess the impact of structural bond areas on flexibility and bending stiffness. Ex. 8 does not feature any structural bonds within the absorbent core structure. Ex. 9 and Ex. 10 have the structural bonds shown in FIG. 4 with the profile shown in FIG. 5. Ex. 8-10 are prepared as described hereafter. Results of the Wet and Dry MD 3 Point Bend Method are shown in Table 7.

TABLE 7

Absorbent Core Structures according to the invention with different Structural
Bond Areas Tested in the Wet and Dry CD and MD 3 Point Bend Method.

| Example | Upper Nonwoven Layer | Inner Core Layer | Lower Nonwoven Layer | Structural Bond Spacing | MD Dry Bending Stiffness (N · mm2) |
|---|---|---|---|---|---|
| Ex. 8 | 50 gsm Resilient Spunlace 6[3] | 175 gsm Fluff[10]/ 70 gsm AGM[9] | 10 gsm SMS Nonwoven[13] | Non-Structural Bonds | 9.8 |
| Ex. 9 | 50 gsm Resilient Spunlace 6[3] | 175 gsm Fluff[10]/ 70 gsm AGM[9] | 10 gsm SMS Nonwoven[13] | 32 mm × 16 mm | 19.2 |
| Ex. 10 | 50 gsm Resilient Spunlace 6[3] | 175 gsm Fluff[10]/ 70 gsm AGM[9] | 10 gsm SMS Nonwoven[13] | 16 mm × 16 mm | 29.6 |

[3]Available as Sawasoft ® 553FC041005 (option 82) from Sandler GmbH (Germany)
[9]Available as Favor SXM9745 from Evonik (Germany)
[10]Available as Item 9E3-COOSABSORB S from Resolute Alabama (USA)
[13]Available as 10 SMS PHILIC from Union Industries SpA. (Italy)

bunched. Comp. Ex. F-L, which are in-market finished products, exhibit a CD Dry Bending Stiffness of 29 to 47.5 N·mm$^2$, demonstrating that the structures are less flexible and less able to conform.

Figure 5:
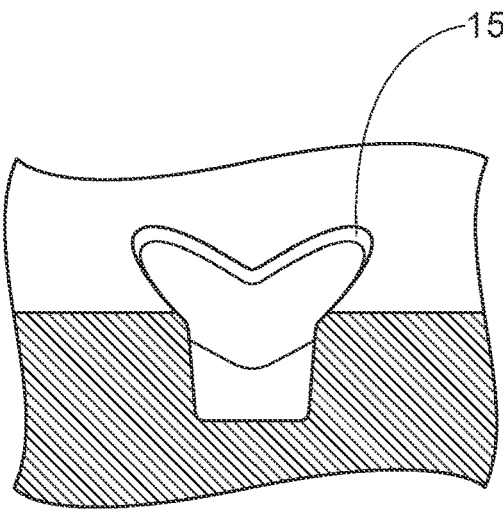
FIG. 5 is a cross section of the structural bond site of FIG. 4.

Without being limited by theory, it is believed that in order to sustain a comfortable shape recovery after compression, sufficient recovery energy is needed to push the absorbent article on the panty back to its pre-compression Table 7 demonstrates the impact of the total structural bond site area and spacing amount. The asymmetric structural bond shape as shown in FIG. 4 and the profile as shown in FIG. 5 has a maximum area of 3.55 mm$^2$. It is found that the MD Dry Bending Stiffness increases with the structural bond area. Ex. 8, which has non-structural bonds, exhibits an MD Dry Bending Stiffness of 9.8 N·mm$^2$. Ex. 9, which has a structural bond spacing of 32 mm×16 mm (a total structural bond site area of 1.38% of the total area of the absorbent core structure), exhibits an MD Dry Bending Stiffness of 19.2 N·mm². Ex. 10, which has a structural bond spacing of 16 mm×16 mm (a total structural bond site area of 3.96% of the total area of the absorbent core structure), exhibits an MD Dry Bending Stiffness of 29.6 N·mm². It is believed that in order to maintain a flexible and conformable absorbent core structure and/or an absorbent article in the front to back (MD) direction of wearing, the absorbent core structure and/or absorbent article can have an MD Dry Bending Stiffness of from about 10 to about 30 N·mm².

The absorbent core structures listed in Table 7 are produced as detailed within the specification. Specifically, the 50 gsm Resilient Spunlace 6 upper nonwoven is first introduced onto the forming drum within the laydown section, and under vacuum, it is drawn into the 3 dimensional pocket shape. A homogeneous stream of the fluff (cellulose) and AGM material is deposited onto the upper nonwoven material directly within the forming station. Prior to entering the forming station, the upper nonwoven is coated with a spray adhesive (Technomelt DM 9036U available from Henkel (Germany), 6 gsm continuous meltblown spirals, 50 mm wide) to provide a stronger connection of the fluff (cellulose) and AGM to the upper nonwoven layer without hindering the flow of liquid into the fluff/AGM mass. On exiting the laydown section, the 10 gsm SMS lower nonwoven web is combined with the nonwoven carrying the homogeneous blend of fluff (cellulose) and AGM layer. This lower nonwoven is precoated with adhesive (Technomelt DM 9036U available from Henkel (Germany)) to enable a perimeter seal (10 gsm meltblown spirals, 20 mm wide on the sides) and in the center a 6 gsm, 50 mm wide continuous meltblown spiral adhesive is applied to better integrate the fluff/AGM mass. Structural bonds as shown in FIG. 4 with the profile shown in FIG. 5 are applied to Ex. 9 and 10. The structural bonds of Ex. 9 have a spacing of 32 mm×16 mm, thereby occupying a total structural bond site area of 1.38% of the total area of the absorbent core structure. The structural bonds of Ex. 10 have a spacing of 16 mm×16 mm, thereby occupying a total structural bond site area of 3.96% of the total area of the absorbent core structure with this structural bond profile. The total area of the absorbent core structure is measured according to the Structural Bond Sites Pattern Spacing and Area Measurement Method. The structural bonds are applied with the same method as described above for Ex. 1-3 and Comp. Ex. A-B.

Combinations/Examples

A. A disposable absorbent article comprising: a topsheet; a backsheet; and an absorbent core structure disposed between the topsheet and the backsheet, wherein the absorbent core structure comprises: (a) an upper nonwoven layer comprising polymer fibers and having a basis weight of from 35 gsm to 85 gsm; (b) a lower nonwoven layer comprising polymer fibers and having a basis weight of from 10 gsm to 40 gsm; and (c) an inner core layer disposed between the upper nonwoven layer and the lower nonwoven layer, wherein the inner core layer comprises from 50% to 85% cellulosic fibers, by weight of the inner core layer, and from 15% to 50% superabsorbent particles, by weight of the inner core layer, and wherein the absorbent core structure has an average density of between 0.045 g/cm3 and 0.15 g/cm3; wherein the inner core layer is contained within the upper nonwoven layer and the lower nonwoven layer by substantially sealing at least a left side region and a right side region of the upper nonwoven layer and the lower nonwoven layer at a perimeter seal.

B. The disposable absorbent article Paragraph A, wherein the absorbent core structure comprises a plurality of structural bond sites; wherein the structural bond sites have a bond area of from 2 mm2 to 5 mm2 as measured according to the Structural Bond Sites Pattern Spacing and Area Measurement Method.

C. The disposable absorbent article of Paragraph B, wherein the total structural bond area of the absorbent core structure is from 0.75% to 4.5% of the absorbent core structure as measured according to the Structural Bond Sites Pattern Spacing and Area Measurement Method.

D. The disposable absorbent article of Paragraphs B-C, wherein the average distance between the structural bond sites is from 10 mm to 32 mm as measured according to the Structural Bond Sites Pattern Spacing and Area Measurement Method.

E. The disposable absorbent article of Paragraphs B-D, wherein the upper nonwoven layer and the lower nonwoven layer are closer together in the Z direction at the structural bond sites but are not melted together.

F. The disposable absorbent article of Paragraphs A-E, wherein the polymer fibers of the upper nonwoven layer are selected from polyethylene terephthalate, polypropylene, polylactic acid, bicomponent fiber comprising polyethylene/polypropylene or polyethylene/polyethylene terephthalate, and combinations thereof.

G. The disposable absorbent article of Paragraphs A-F, wherein the polymer fibers of the lower nonwoven layer are selected from polyethylene terephthalate, polypropylene, polylactic acid, bicomponent fiber comprising polyethylene/polypropylene or polyethylene/polyethylene terephthalate, and combinations thereof.

H. The disposable absorbent article of Paragraphs A-G, wherein the absorbent article has a Dry Caliper between about 2.0 mm and about 6.0 mm as measured according to the Wet and Dry CD and MD 3-Point Method.

I. The disposable absorbent article of Paragraphs A-H, wherein the polymer fibers of the upper nonwoven layer have a fiber length of from 10 mm to 100 mm, preferably from 20 mm to 50 mm.

J. The disposable absorbent article of Paragraphs A-I, wherein the polymer fibers of the upper nonwoven layer have a fiber diameter of from 2.0 DTex to 10 DTex and the polymer fibers of the lower nonwoven layer have a fiber diameter of from 1.7 DTex to 5 DTex.

K. The disposable absorbent article of Paragraphs A-J, wherein the polymer fibers of the upper nonwoven layer comprise from 70 to 100% synthetic fibers, and from 0 to 40% regenerated cellulosic fibers comprising rayon.

L. The disposable absorbent article of Paragraphs A-K, wherein the upper nonwoven layer has a Tensile Stiffness of from 0.3 to 1.6 N/mm as measured according to the CD Cyclic Elongation to 3% Strain Method, and a Strain to Break of from 10% to 50%, preferably from 20% to 40%, as measured according to the Strain to Break Method.

M. The disposable absorbent article of Paragraphs A-L, wherein the upper nonwoven layer has a Tensile Stiffness of from about 0.3 N/mm to about 1.0 N/mm as measured according to the CD Cyclic Elongation to 3% Strain Method.

N. The disposable absorbent article of Paragraphs A-M, wherein the lower nonwoven layer has a Permanent Strain of 0.005 mm/mm to 0.013 mm/mm as measured according to the CD Cyclic Elongation to 3% Strain Method.

O. The disposable absorbent article of Paragraphs A-N, wherein the absorbent article has a Light Touch Rewet value of from 0 to 0.15 grams as measured according to the Light Touch Rewet Method.

P. The disposable absorbent article of Paragraphs A-O, wherein the upper nonwoven layer is an air through bonded nonwoven or a hydroentangled nonwoven.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross refer-enced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a topsheet;
a backsheet; and
an absorbent core structure disposed between the topsheet and the backsheet, wherein the absorbent core structure comprises:
a. an upper nonwoven layer comprising polymer fibers and having a basis weight of from about 35 gsm to about 85 gsm;
b. a lower nonwoven layer comprising polymer fibers and having a basis weight of from about 10 gsm to about 40 gsm; and
c. an inner core layer disposed between the upper non-woven layer and the lower nonwoven layer, wherein the inner core layer comprises from about 50% to about 85% cellulosic fibers, by weight of the inner core layer, and from about 15% to about 50% superabsorbent particles, by weight of the inner core layer, and wherein the absorbent core structure has an average density of between about 0.045 g/cm3 and about 0.15 g/cm3;
wherein the inner core layer is contained within the upper nonwoven layer and the lower nonwoven layer by substantially sealing at least a left side region and a right side region of the upper nonwoven layer and the lower nonwoven layer at a perimeter seal; and
wherein the absorbent core structure comprises a plurality of structural bond sites, wherein the structural bond sites comprise at least the upper nonwoven layer and the inner core layer throughout the structural bond site.

2. The disposable absorbent article of claim 1, wherein the upper nonwoven layer has a Tensile Stiffness of from about 0.3 N/mm to about 1.6 N/mm as measured according to the CD Cyclic Elongation to 3% Strain Method, and a Strain to Break of greater than 10% as measured according to in the Strain to Break Method.

3. The disposable absorbent article of claim 1, wherein the upper nonwoven layer has a Tensile Stiffness of from about 0.3 N/mm to about 1.6 N/mm as measured according to the CD Cyclic Elongation to 3% Strain Method, and a Strain to Break of from about 10% to about 50% as measured according to the Strain to Break Method.

4. The disposable absorbent article of claim 2, wherein the upper nonwoven layer has a Tensile Stiffness of from about 0.3 N/mm to about 1.0 N/mm as measured according to the CD Cyclic Elongation to 3% Strain Method.

5. The disposable absorbent article of claim 1, wherein the lower nonwoven layer has a Permanent Strain of about 0.005 mm/mm to about 0.013 mm/mm as measured according to the CD Cyclic Elongation to 3% Strain Method.

6. The disposable absorbent article of claim 1, wherein the polymer fibers of the upper nonwoven layer are selected from polyethylene terephthalate, polypropylene, polylactic acid, bicomponent fiber comprising polyethylene/polypro-pylene or polyethylene/polyethylene terephthalate, and combinations thereof.

7. The disposable absorbent article of claim 1, wherein the polymer fibers of the lower nonwoven layer are selected from polyethylene terephthalate, polypropylene, polylactic acid, bicomponent fiber comprising polyethylene/polypro-pylene or polyethylene/polyethylene terephthalate, and combinations thereof.

8. The disposable absorbent article of claim 1, wherein the polymer fibers of the upper nonwoven layer have a fiber length of from about 10 mm to about 100 mm.

9. The disposable absorbent article of claim 1, wherein the polymer fibers of the upper nonwoven layer have a fiber diameter of from about 2.0 Dtex to about 10 Dtex, and the polymer fibers of the lower nonwoven layer a fiber diameter of from about 1.7 Dtex to about 5 Dtex.

10. A disposable absorbent article comprising:
a topsheet;
a backsheet; and
an absorbent core structure disposed between the topsheet and the backsheet,
wherein the absorbent core structure has a front, middle, and back region and comprises:
a. an upper nonwoven layer comprising polymer fibers and having a basis weight of from about 35 gsm to about 85 gsm;
b. a lower nonwoven layer comprising polymer fibers and having a basis weight of from about 10 gsm to about 40 gsm; and
c. an inner core layer disposed between the upper non-woven layer and the lower nonwoven layer, wherein the inner core layer comprises a mixture of cellulosic fibers and superabsorbent particles;
wherein the absorbent core structure comprises a plurality of structural bond sites; wherein the structural bond sites comprise at least the upper nonwoven layer and the inner core layer throughout the structural bond site, wherein the structural bond sites have a bond area of from about 2 mm$^2$ to about 5 mm$^2$; and wherein the total structural bond area of the absorbent core structure is from about 0.75% to about 4.5% of the absorbent core structure as measured according to the Structural Bond Sites Pattern Spacing and Area Measurement Method.

11. The disposable absorbent article of claim 10, wherein the average distance between the structural bond sites is from about 10 mm to about 32 mm as measured according to the Structural Bond Sites Pattern Spacing and Area Measurement Method.

12. The disposable absorbent article of claim 10, wherein the inner core layer has an average density of between 0.045 g/cm³ and 0.15 g/cm³.

13. The disposable absorbent article of claim 10, wherein the inner core layer is contained within the upper nonwoven layer and the lower nonwoven layer by substantially sealing at least a left side region and a right side region of the upper nonwoven layer and the lower nonwoven layer at a perimeter seal.

14. The disposable absorbent article of claim 10, wherein the upper nonwoven layer and the lower nonwoven layer are closer together in the Z direction at the structural bond sites but are not melted together.

15. The disposable absorbent article of claim 10, wherein the absorbent article has a Dry Caliper between about 2.0 mm and about 6.0 mm as measured according to the Wet and Dry CD and MD 3-Point Method.

16. The disposable absorbent article of claim 10, wherein the polymer fibers of the upper nonwoven layer and the polymer fibers of the lower nonwoven layer are different.

17. The disposable absorbent article of claim 10, wherein the polymer fibers of the upper nonwoven layer and the polymer fibers of the lower nonwoven layer are the same.

18. The disposable absorbent article of claim 10, wherein the polymer fibers of the upper nonwoven layer comprise from about 70% to about 100% synthetic fibers, and from about 0% to about 40% regenerated cellulosic fibers comprising rayon.

19. The disposable absorbent article of claim 10, wherein the inner core layer comprises from about 55% to about 80% cellulosic fibers, by weight of the inner core layer, and from about 25% to about 35% superabsorbent particles, by weight of the inner core layer.

20. The disposable absorbent article of claim 1, wherein the upper nonwoven layer and the inner core layer are intermingled within the structural bond sites.

* * * * *